(12) United States Patent
Gerold et al.

(10) Patent No.: US 7,210,598 B2
(45) Date of Patent: May 1, 2007

(54) AUTHOMATED PILL-DISPENSING APPARATUS

(75) Inventors: William O. Gerold, Bridgman, MI (US); William J. Gerold, Bridgman, MI (US)

(73) Assignee: Microfil, LLC, Bridgman, MI (US)

( * ) Notice: Subject to any disclaimer, the term of this patent is extended or adjusted under 35 U.S.C. 154(b) by 0 days.

(21) Appl. No.: 10/160,970

(22) Filed: May 31, 2002

(65) Prior Publication Data

US 2003/0222091 A1 Dec. 4, 2003

(51) Int. Cl.
*G07F 11/00* (2006.01)

(52) U.S. Cl. .................................. 221/123; 221/220

(58) Field of Classification Search ............... 221/123, 221/124, 133, 200, 9, 13, 241, 207, 246, 221/247, 251; 700/241, 242, 244; 198/766, 198/769, 771; 53/500, 52, 55, 495, 411, 131.4, 53/247; 705/2, 3
See application file for complete search history.

(56) References Cited

U.S. PATENT DOCUMENTS

| | | | | |
|---|---|---|---|---|
| 3,227,500 A | * | 1/1966 | Sawrey | 312/35 |
| 3,305,067 A | * | 2/1967 | Mayer | 198/383 |
| 3,502,382 A | * | 3/1970 | Rainey | 312/42 |
| 4,546,901 A | * | 10/1985 | Buttarazzi | 221/10 |
| 4,651,868 A | * | 3/1987 | Sticht | 198/540 |
| 4,844,236 A | * | 7/1989 | Kraus | 198/690.2 |
| 5,348,061 A | * | 9/1994 | Riley et al. | 141/104 |
| 5,473,703 A | * | 12/1995 | Smith | 382/143 |
| 5,511,690 A | * | 4/1996 | Calhoun et al. | 221/197 |
| 5,852,911 A | * | 12/1998 | Yuyama et al. | 53/168 |
| 5,901,876 A | * | 5/1999 | Yuyama et al. | 221/133 |
| 5,967,294 A | * | 10/1999 | Patterson et al. | 198/763 |
| 5,988,858 A | * | 11/1999 | Yuyama et al. | 700/230 |
| 6,131,765 A | * | 10/2000 | Barry et al. | 221/264 |
| 6,145,700 A | * | 11/2000 | Takahashi et al. | 221/133 |
| 6,179,117 B1 | * | 1/2001 | Gilman | 198/751 |
| 6,181,982 B1 | * | 1/2001 | Yuyama et al. | 700/236 |
| 6,189,683 B1 | * | 2/2001 | Svejkovsky et al. | 198/769 |
| 6,206,235 B1 | * | 3/2001 | Green | 221/251 |
| 6,286,658 B1 | * | 9/2001 | Hufford | 198/766 |
| 6,298,978 B1 | * | 10/2001 | Rosenstrom | 198/753 |
| 6,308,109 B1 | * | 10/2001 | Yuyama et al. | 700/228 |
| 6,394,308 B1 | * | 5/2002 | Yuyama et al. | 221/265 |
| 6,415,913 B2 | * | 7/2002 | Sleppy et al. | 198/766 |
| RE37,829 E | * | 9/2002 | Charhut et al. | 700/216 |
| 6,449,927 B2 | * | 9/2002 | Hebron et al. | 53/501 |
| 6,505,093 B1 | * | 1/2003 | Thatcher et al. | 700/216 |
| 6,611,733 B1 | * | 8/2003 | De La Huerga | 700/236 |
| 6,631,799 B2 | * | 10/2003 | Samson | 198/771 |

OTHER PUBLICATIONS

Discloses information off the internet concerning a prior art vibrating pill feeder made by FMC Technologies.
Discloses information off the internet concerning a prior art vibrating pill feeder made by Meyer Machine Co.

* cited by examiner

*Primary Examiner*—Patrick Maekey
*Assistant Examiner*—Matthew J. Kohner
(74) *Attorney, Agent, or Firm*—Price, Heneveld, Cooper, DeWitt & Litton LLP

(57) ABSTRACT

An under-counter portable automatic pill-dispensing apparatus includes a double array of storage units for storing pills in bulk, a retriever between the two arrays for retrieving selected storage units, and a pill-dispensing module for unloading pills into a vial. The storage units each include an outer container, a track positioned in a bottom of the outer container, and a hopper movably positioned within the outer container for movement toward and away from the track. The pill-dispensing module includes an oscillator for the track, a pill counter, and a lift for raising and lowering the hopper to control flow of pills. A prescription information station is provided including a computer for receiving patient prescription information, a printer for printing a label for the vial and for applying the label to the vial, bar code scanners for verification, and distributed controllers for operating the various components.

20 Claims, 29 Drawing Sheets

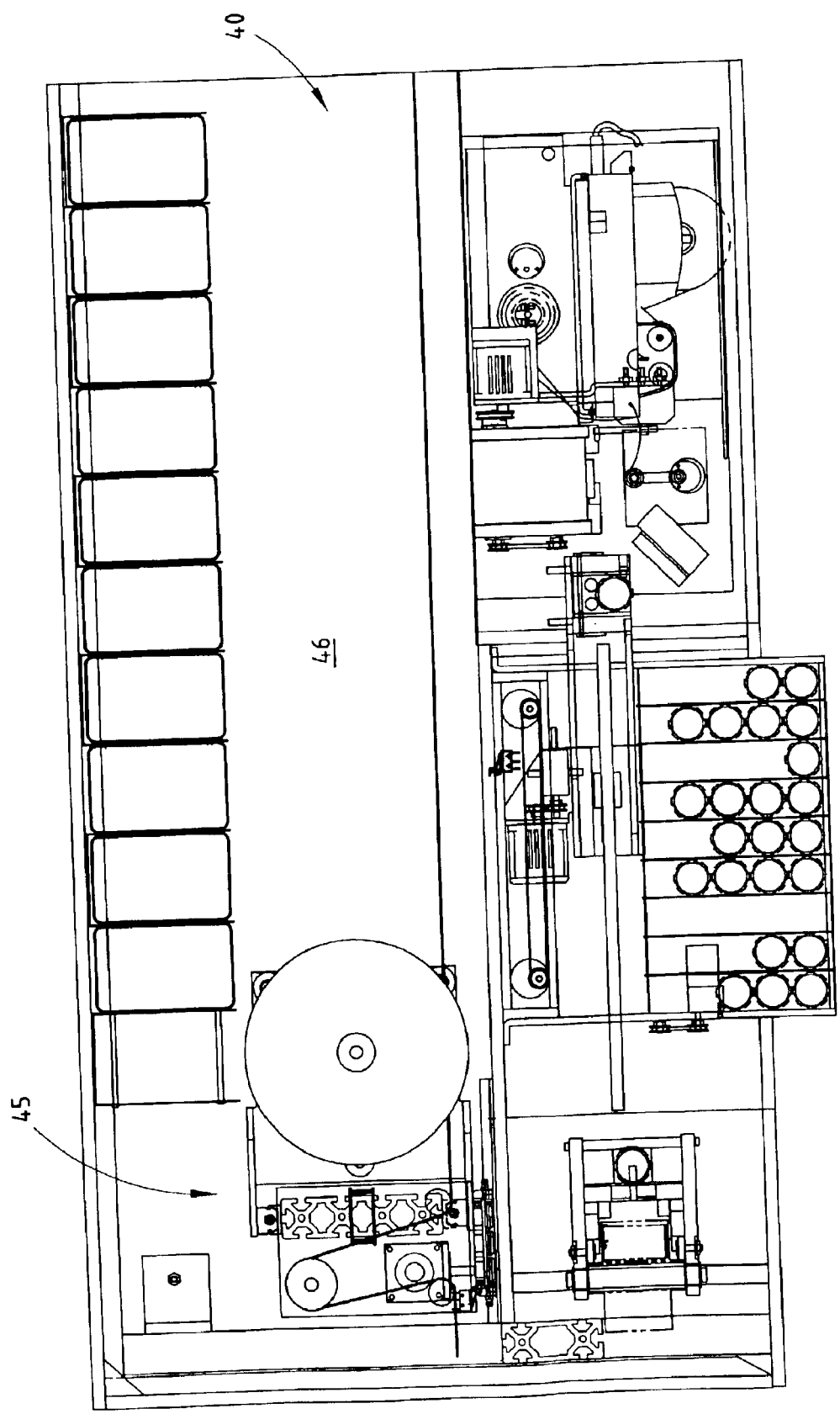

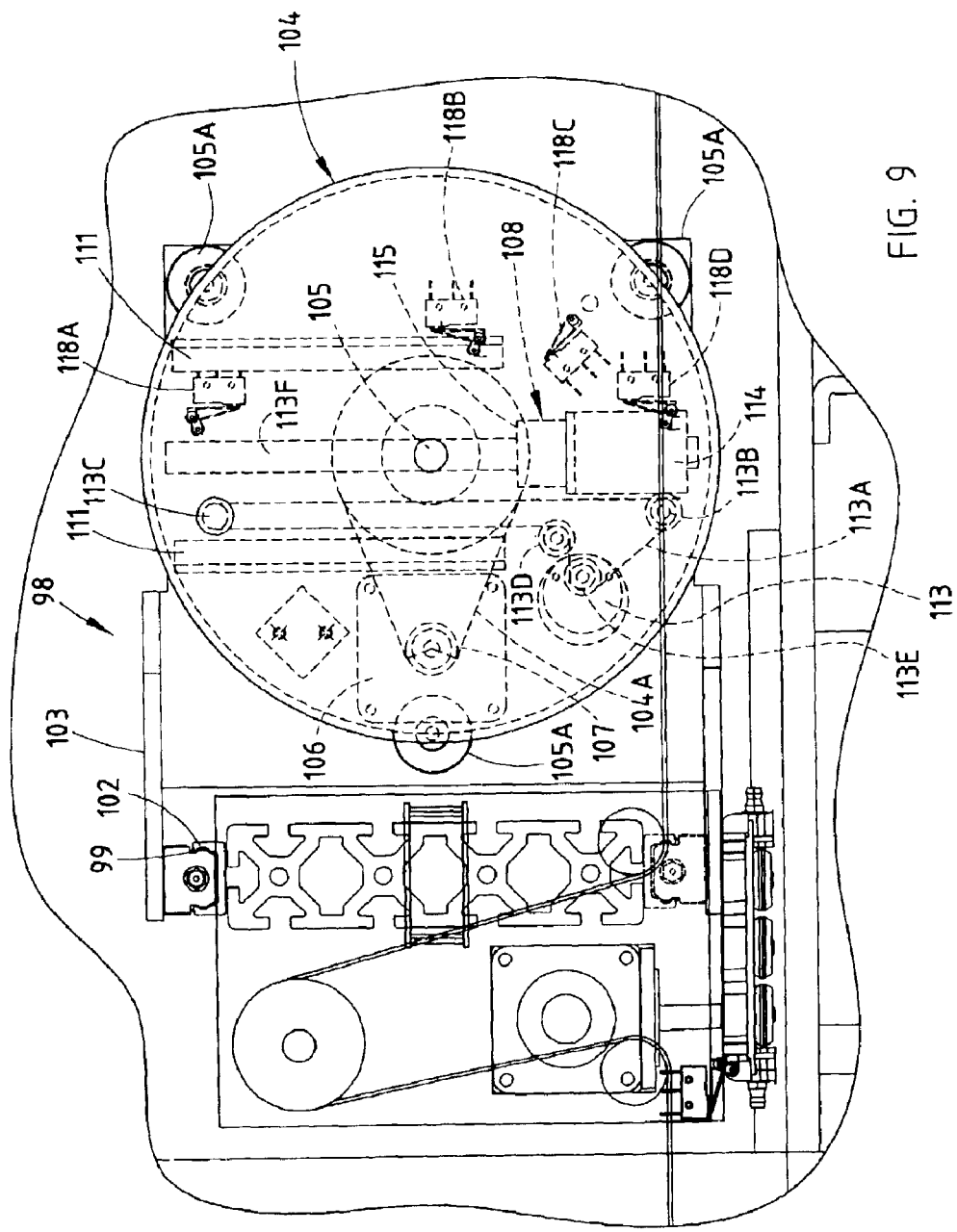

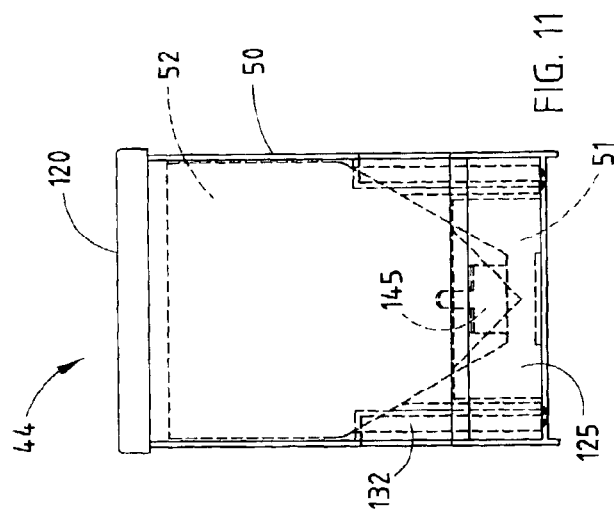
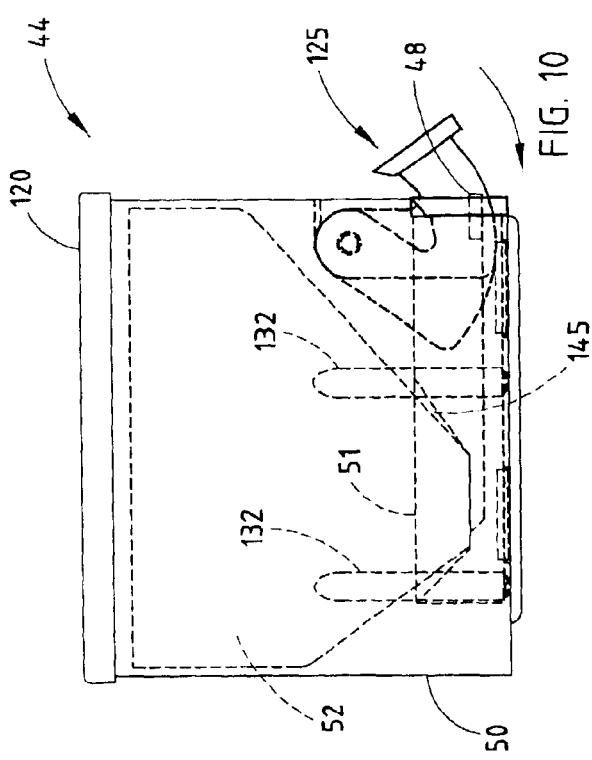
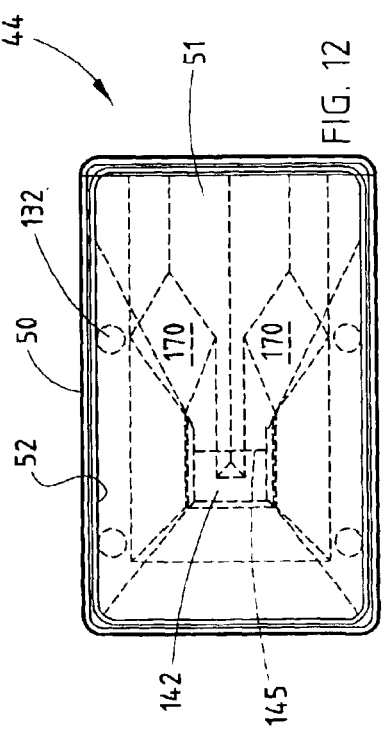

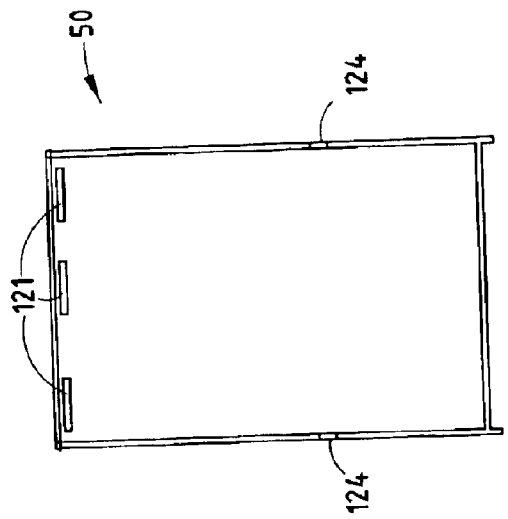
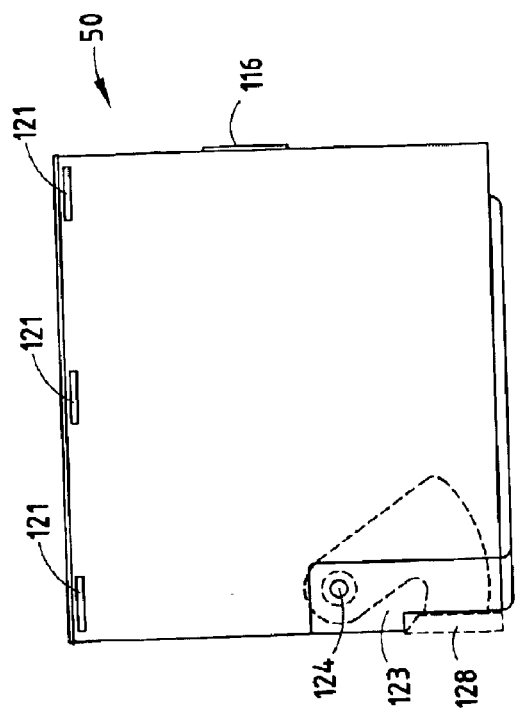
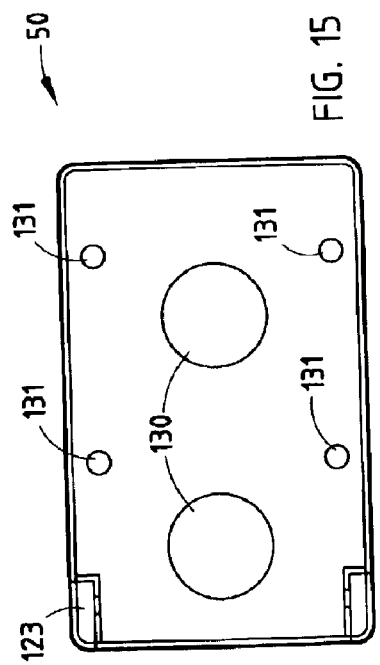
FIG. 14
FIG. 13
FIG. 15

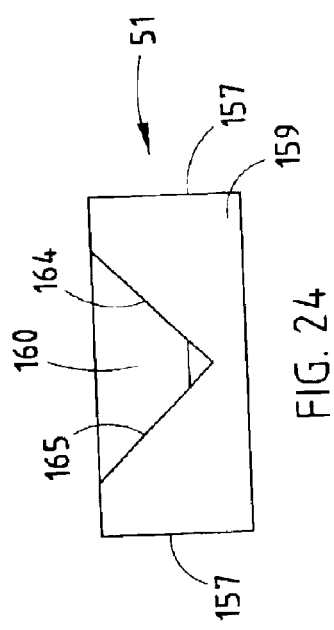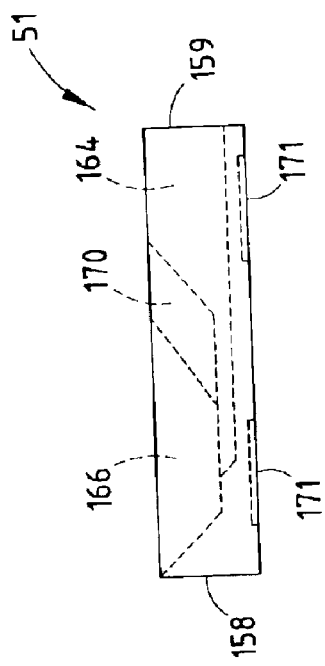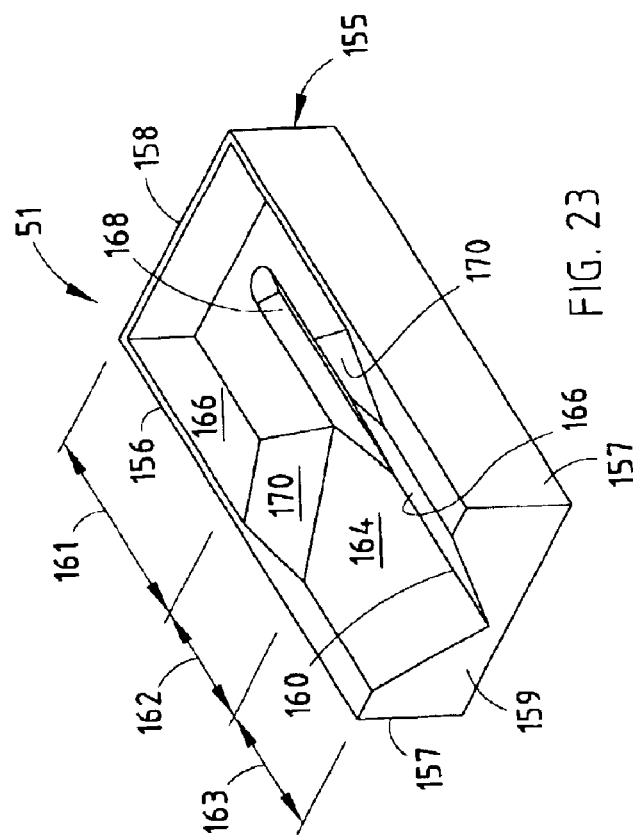

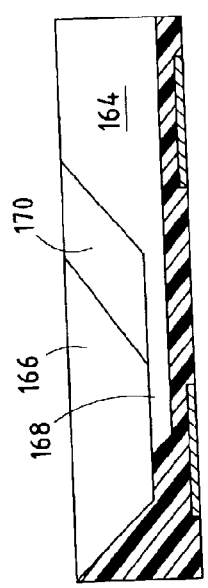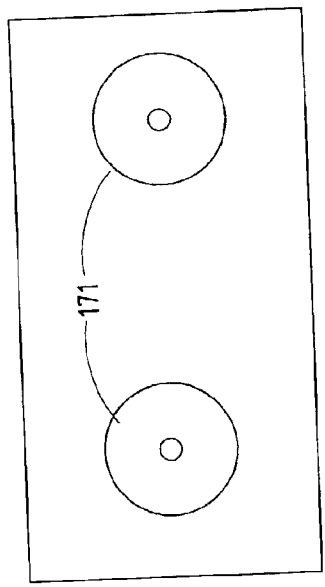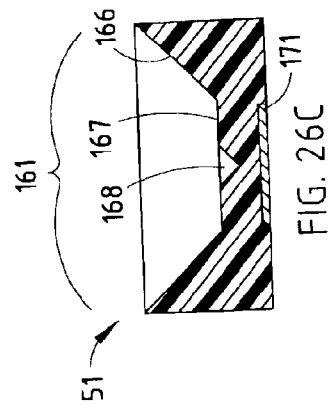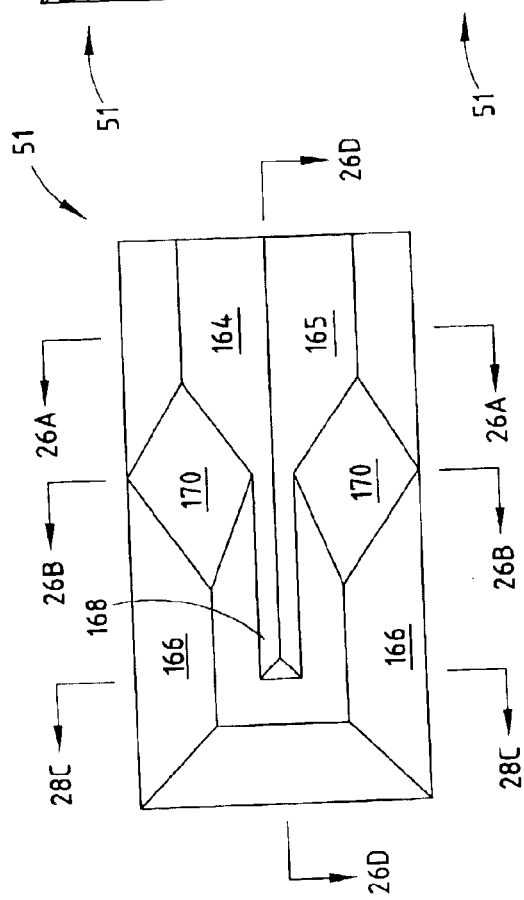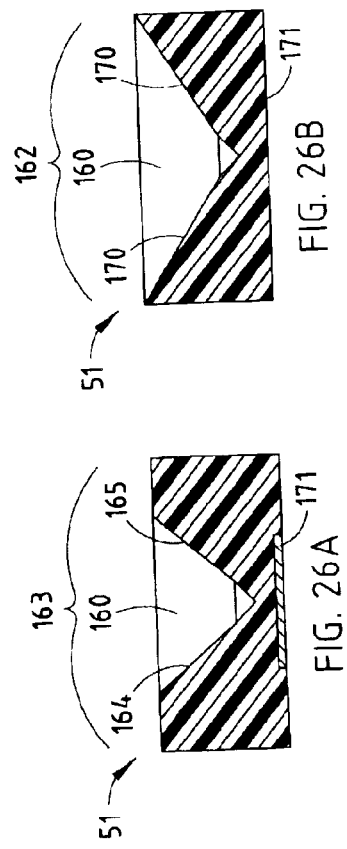

AUTHOMATED PILL-DISPENSING APPARATUS

BACKGROUND

The present invention relates to automated pill-dispensing apparatus, and more particularly relates to a modular compact pill-dispensing apparatus for automated dispensing of pills in retail pharmacy environments.

There is a need to optimize use of pharmacist time, since the time of a pharmacist is expensive. In particular, there is a need to let a pharmacist use his/her expertise without burdening him/her with mundane work such as counting pills and placing them in bottles. Further, it is desirable to reduce the amount of time a pharmacist spends walking around the pharmacy area, not only to reduce wasted time but also to reduce fatigue of the pharmacist as the day progresses.

There is further a need to optimize the density of storage of pills. In many pharmacies, pills are stored in every nook and cranny possible. Also, the logistics of stored pills relative to the customers and to the pharmacist, should preferably be improved. As part of the logistics, it is important to keep in mind the security of pills, the cleanliness, and the ability to keep the areas clean, especially in the retail environment where cleanliness can be a problem.

Another concern is equipment. Any automated equipment must be compact, flexible, and adjustable for optimally handling different types of pills. However, standardized components should preferably be used, including components that are easily serviceable, fixable on site, reliable, robust, durable, low maintenance, simple to operate, low-cost, and that require a relatively lower capital investment. Further, any programmed features must be configured to optimize quality control and efficiency and control of the operation.

There is a need to increase the accuracy and reduce the errors in filling prescriptions. As part of this, there is a need to improve pill handling and accuracy of pills counts. These are difficult problems, because of the difference in sizes and shapes of pills make pill handling difficult. At the same time, different sizes and shapes of pills are required so that a pharmacist (and patient) can recognize wrong pills. Further, pill handling must deal with quality control issues, including the fact that pill counting is a relatively mundane and boring task.

There is a need to provide adjustability and reliability in pill handling equipment. There is a need to be able to adjust for different pills on site without requiring customized specially-ordered equipment or part. There is a need to reliably and accurately drop pills into vials, while still providing the flexibility that will allow pharmacists to still provide the human control required for dispensing medicines critical to the health of patients, Another issue is security. Any automated equipment should provide good security and resistance to theft and tampering. As part of this software and programming, it is desirable to provide a refill procedure that not only controls refilling and prevents errors in filling storage units with wrong pills, but also that keeps track of pill counts.

Accordingly, an automated apparatus is desired that provides the advantages noted above and that solves the disadvantages.

SUMMARY OF THE PRESENT INVENTION

In one aspect of the present invention, a pill-dispensing apparatus for automatically dispensing solid pills includes a plurality of storage units for storing pills in bulk, each storage unit including an outer container, a track positioned in a bottom of the outer container, and a hopper movably positioned within the outer container for movement toward and away from the track. The apparatus further includes a pill-dispensing module including a dock for receiving and holding a selected one of the storage units, a drive unit for oscillating the track to motivate the pills from the hopper and along the track, a pill counter for counting pills dispensed from the track, and a lift for raising and lowering the hopper to vary a gap between the hopper and the track to control flow and to assist in motivating pills to fall from the hopper to the track.

In a narrower aspect, the apparatus includes a retriever for retrieving a selected one of the storage units based on prescription information and for positioning the selected one storage unit in the pill-dispensing module. In another narrower aspect, a vial handler is provided for holding a vial under the pill-dispensing module for receiving the dispensed pills. In yet another narrower aspect, a prescription information station is provided including a computer for receiving patient prescription information. In one narrower aspect, a printer and applicator are provided for printing a label for the vial and for applying the label to the vial. In still another narrower aspect, a control system, including several independent controllers or computers, is provided for operating the pill-dispensing module, the retriever, the vial handler, and the printer.

In another aspect of the present invention, a pill-dispensing apparatus for automatically dispensing solid pills includes an outer container, a track positioned at a bottom of the outer container, and a hopper movably positioned within the outer container for movement toward and away from the track. The apparatus further includes a dock for holding the storage unit, a vibrator (also called "oscillator") for vibrating the track to motivate the pills along the track, and a lift for lifting the hopper to increase a gap between the track and the hopper when pills bridge up and stop moving along the track.

In another aspect of the present apparatus, a bulk storage unit useful for automatically dispensing solid pills includes an outer container with parallel first walls, a linear track adapted to feed singulated pills along its length and that is positioned in a bottom of the outer container, and a hopper movably positioned within the outer container for movement toward and away from the track, the hopper having second walls positioned parallel and close to the first walls.

In still another aspect of the present invention, a bulk storage unit useful for automatically dispensing solid pills includes a linear track adapted to feed singulated pills along its length when pills in bulk are fed onto a leading end of the track, a hopper having an opening positioned over the track for feeding pills onto the leading end of the track, the hopper including at least one flange, and an adjustable gate movably attached to the flange and adjustable to change a size of a gap between the gate and the track, for adjustably controlling movement of pills along the track.

In yet another aspect of the present invention, a bulk storage unit useful for automatically dispensing solid pills includes a track having a length, an upstream end and a downstream end, the track being adapted to feed pills along its length in a longitudinal direction when the track is vibrated. A storage unit includes a hopper positioned over the track and having an opening for dropping pills onto the upstream end, the storage unit including a door movable between an open position permitting singulated pills to drop off the downstream end and a closed position preventing pills from dropping off the track. The door, when close to the closed position and being moved to the closed position, moving parallel the longitudinal direction so that any pills handing partially off the downstream end are pushed back onto the track as the door comes to rest in the closed position.

In another aspect of the present invention, a track useful for feeding solid pills along its length includes a solid member having a top surface defining a horizontal plane. The top surface has a groove formed therein that extends from an upstream end of the solid member across a middle section of the solid member to a downstream end of the solid member and further that extends to an edge of the solid member at the downstream end. The groove in the downstream end defines a well-defined "V" shape with first angled side surfaces that are adapted to convey singulated pills one at a time off the edge of the downstream end. The groove in the upstream end defines an enlarged shape with second angled side surfaces shaped to store pills but also slidingly convey pills flowing onto the upstream end toward a center of the groove. The groove in the middle section is formed from third angled side surfaces that extend at compound angles to the first and second angled side surfaces to form a transition pocket. The transition pocket redistributes bunched-up pills as the bunched-up pills travel from the upstream end into the middle section such that it unbunches the pills, and then centers and singulates the pills as the unbunched pills travel out of the transition pocket in the middle section to the downstream end.

In the another aspect of the present invention, a pill-dispensing apparatus for automatically dispensing solid pills includes a mobile frame on wheels, a plurality of storage units movably stored on the frame for storing pills in bulk, and an x-y-z direction retriever module on the frame for retrieving the storage units one at a time based on prescription information. A pill-dispensing module on the frame includes a dock for receiving and holding a selected one of the storage units and for dispensing pills from the selected one storage unit. The retriever is adapted to position the selected one storage unit in the pill-dispensing module for dispensing pills and then is adapted to replace the selected one storage unit in its storage position on the frame. A vial handler module is provided on the frame for holding a vial under the pill-dispensing module for receiving the dispensed pills. A controller operates the pill-dispensing module, the retriever module, and the vial handler module.

In another aspect of the present invention, a pill-dispensing apparatus for automatically dispensing solid pills includes, in combination, a countertop and countertop support adapted to position the countertop above a floor surface at a height suitable for use by a pharmacist standing and working adjacent the countertop, the countertop having a top surface suitable for handling pills and filling prescriptions, and further the opposing sides of the countertop being open so that the pharmacist can communicate with and give prescriptions to customers on a side of the countertop opposite from the pharmacist. A dispensing apparatus is provided for automatically dispensing pills from bulk containers to vials pursuant to the prescriptions, the dispensing apparatus including a plurality of bulk storage units, a retriever for selecting one of the storage units, a dispensing station for dispensing pills from the selected storage unit, a vial handler for collecting the dispensed pills, and a labeler, all of which are positioned under the countertop.

In yet another aspect of the present invention, a pill-dispensing apparatus for automatically dispensing solid pills includes a frame with storage locations. A plurality of storage units are movably stored in respective ones of the storage locations, the storage units being adapted to hold pills in bulk, the storage units having a depth and being arranged in first and second vertical parallel planes with a space therebetween at least as deep as the depth of the storage units. An x-y-z direction retriever module is operably mounted on the frame for movement in the space, the retriever module including a carrier adapted to carry a selected one of the storage units, the retriever further including first, second and third actuators operable to move the retriever in x, y, and z orthogonal directions, respectively, and further including a coupling device operable to grip the selected one storage unit as the selected one storage unit is pulled from its respective storage location onto the carrier. A pill-dispensing module on the frame includes a dock for receiving and holding the selected one of the storage units and a pill-dispensing mechanism for dispensing pills from the selected one storage unit. A controller is operably connected to the actuators, the gripper, and the pill-dispensing mechanism for controlling the same.

In still another aspect of the present invention, a method of dispensing prescriptions comprises steps of providing bulk storage of pills in storage units under a countertop and above a floor surface, automatically retrieving selected ones of the storage units and then automatically dispensing pills from the selected storage units into vials, the steps of retrieving and dispensing both being performed automatically and under the countertop, and presenting vials filled with dispensed pills to a person standing adjacent the countertop.

In still another aspect of the present invention, a method of automatically dispensing solid pills, comprises steps of providing an outer container with parallel first walls, a linear track in a bottom of the container that is adapted to feed singulated pills along its length, and a hopper movably positioned within the outer container, the hopper being filled with pills and having an opening with pills flowing through the opening onto the track. The method further includes moving one of the hopper and the track to change a distance from the opening to the track to cause pills that have bridged and bunched up in the opening to become unbunched.

In still another aspect of the present invention, a method of automatically refilling containers of solid pills in bulk, comprises steps of providing bulk storage of pills in a plurality of storage units stored under a countertop and above a floor surface; sensing that one of the storage units is empty and unable to dispense pills, and automatically retrieving the empty storage unit and presenting the retrieved storage unit to a pharmacist for filling with a new supply of pills.

An object of the present invention is to provide a faster, more efficient apparatus that provides and utilizes a higher density of product storage in a retail prescription environment.

Another object is to provide an under-counter, mobile device that can be readily moved out for repair yet also readily moved to a well-hidden, highly-convenient use position under a countertop.

These and other aspects, objects, and features of the present invention will be understood and appreciated by those skilled in the art upon studying the following specification, claims, and appended drawings.

BRIEF DESCRIPTION OF DRAWINGS

FIG. 4A is an enlarged partial view of the left hand-portion of FIG. 4;

FIGS. 8–9 are front and top views of the retriever module shown in FIG. 7;

FIGS. 10–12 are side, front, and top views of the storage unit shown in FIG. 7;

FIGS. 13–15 are side, top, and bottom views of the outer container shown in FIG. 12A;

FIGS. 23–27 are perspective, front, side, top, and bottom views of the pill track shown in FIG. 12A;

FIGS. 26A–26D are cross-sectional views taken along the lines 26A–26A, 26B–26B, 26C–26C, and 26D–26D in FIG. 26;

FIG. 30 shows the internal hopper raised so that the gate is very open in a large-gap position;

DETAILED DESCRIPTION OF PREFERRED EMBODIMENTS

Figure 1:
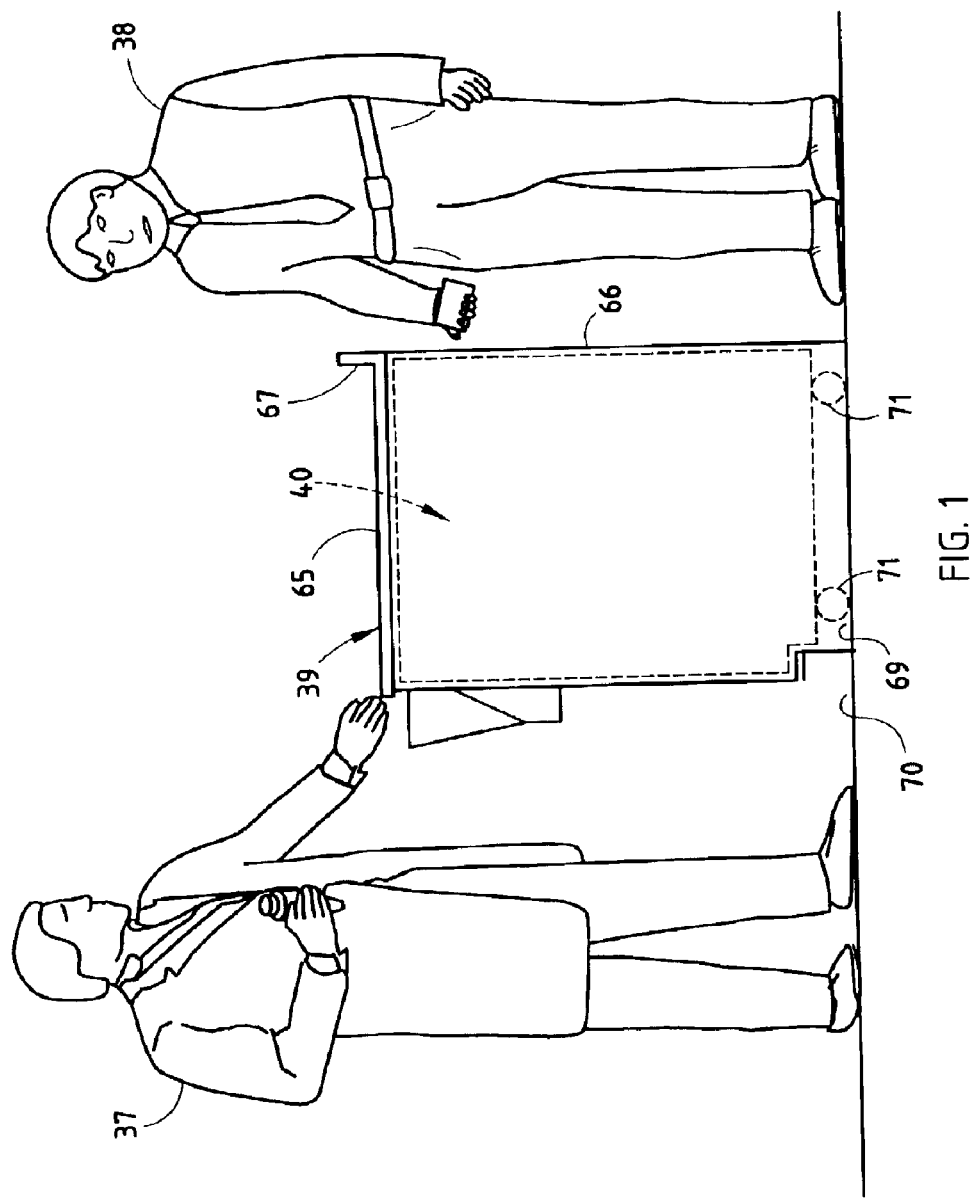
FIG. 1 discloses a side view of a pharmacist countertop, including the present apparatus under the countertop.
Figure 2:
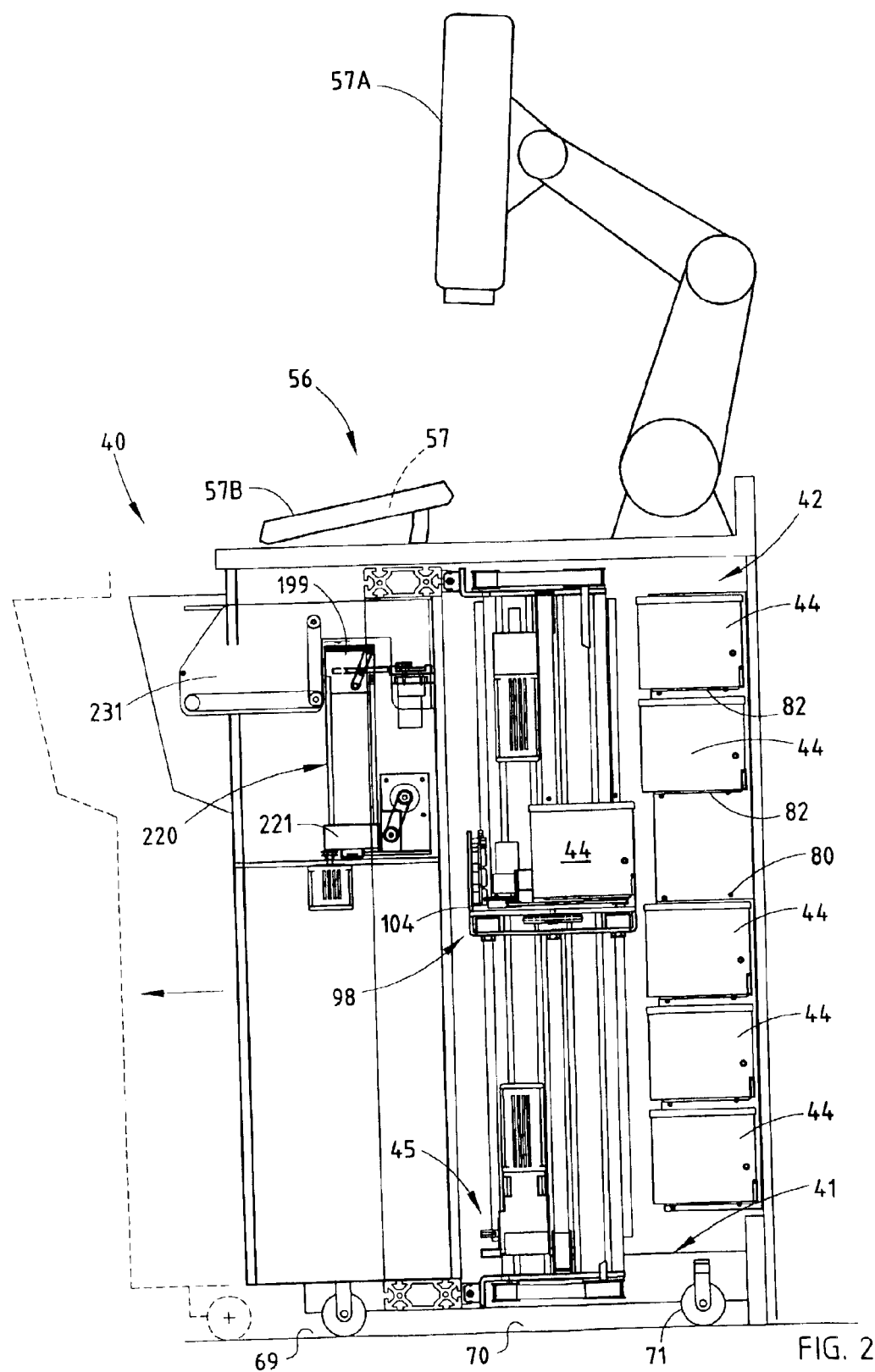
FIGS. 2–4 are side, front, and top orthogonal views of the apparatus shown in FIG. 1, with panels removed to better show the apparatus.
Figure 4:
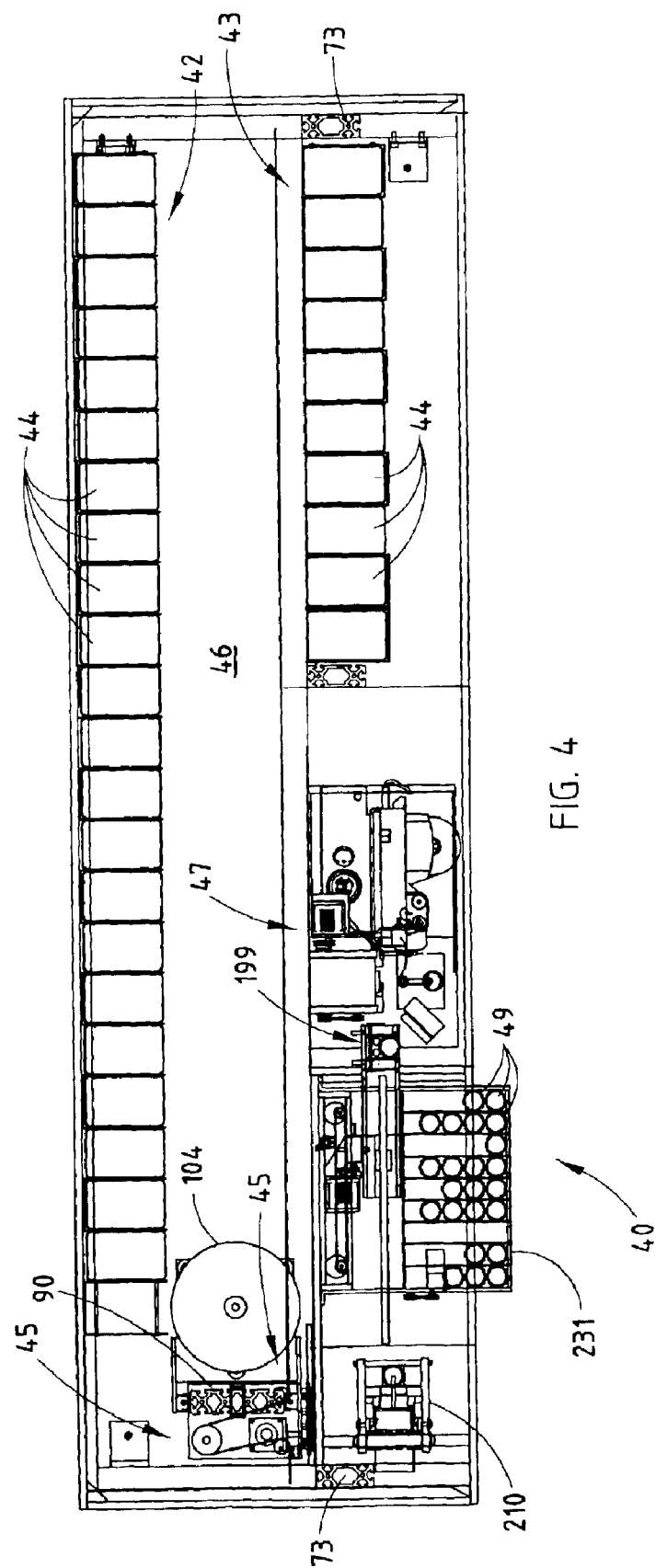
Figure 12A:
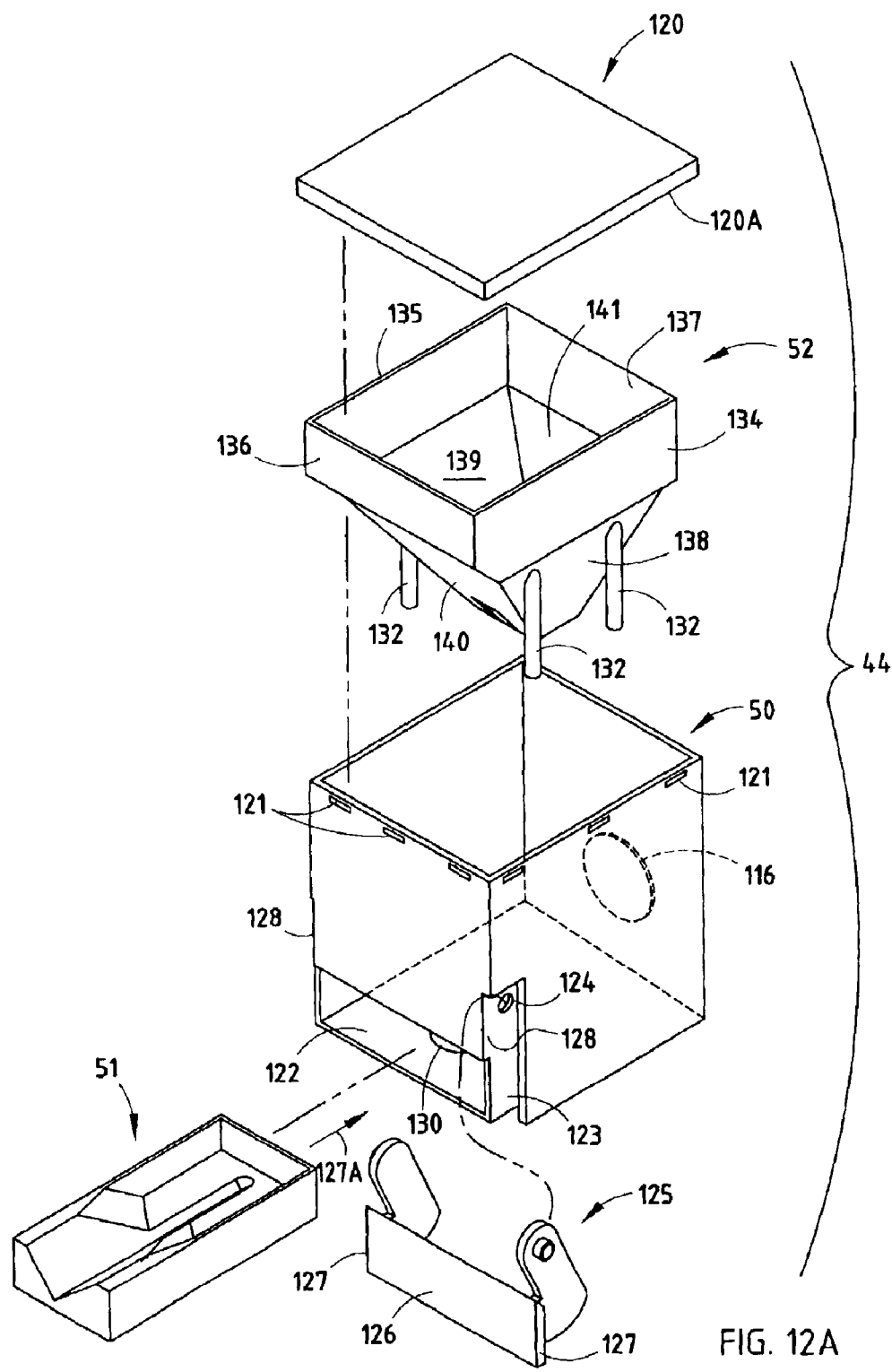
FIG. 12A is an exploded perspective view of the storage unit shown in FIG. 10.
Figure 33:
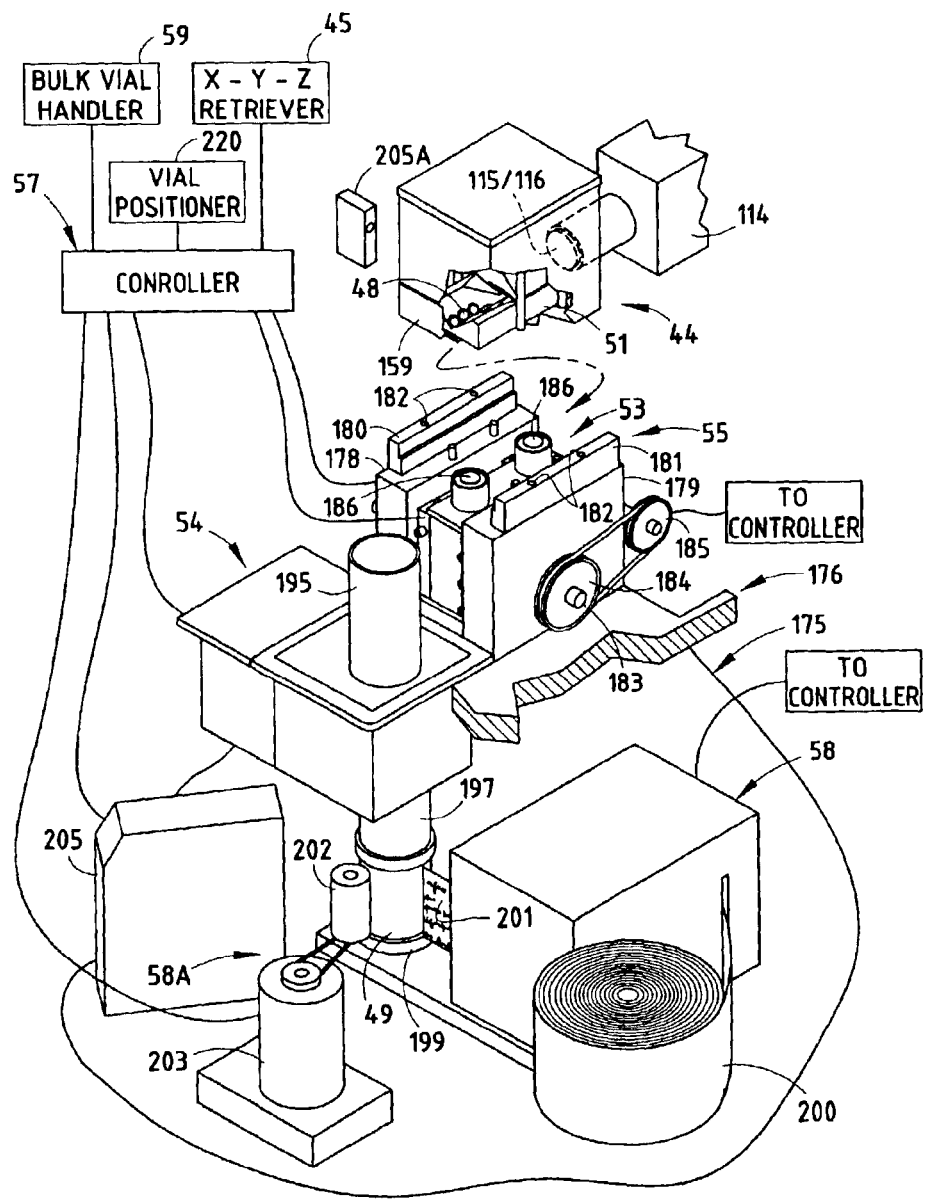
FIG. 33 is a perspective view of the pill-dispensing module.

A portable automatic pill-dispensing apparatus 40 (FIG. 1) includes a wheeled mobile frame 41 located under a countertop 39 in a position allowing a pharmacist 37 to serve a customer 38 and simultaneously fill prescriptions while standing at the countertop 39. The apparatus 40 carries two parallel stacked arrays 42 and 43 (FIG. 4) of storage units 44 for storing pills, tablets, capsules, and similar medication units 48 (hereafter called "pills") in bulk, an x-y-z retriever module 45 (FIG. 7) positioned in an aisle 46 between the two arrays for retrieving selected ones of the storage units 44, and a pill-dispensing module 47 (FIG. 33) for unloading pills 48 into vials 49. The storage units 44 (FIG. 12A) each include a rectangular outer container 50, a vibrating pill track 51 (also called a "feed block" or "drive unit") positioned in a bottom of the outer container 50, and a hopper 52 movably positioned within the outer container 50 for vertical movement toward and away from the track 51. The pill-dispensing module 47 (FIG. 33) includes a vibrator or oscillator 53 for the track 51, a pill counter 54, and a lift 55 for lifting the hopper 52 to break bunched-up and "bridged" pills 48. A prescription information station 56 (FIG. 2) is provided including a computer 57, screen or monitor 57A and keyboard 57B for storing, viewing, and inputting patient prescription information, a printer 58 and applicator 58A (FIG. 33) for printing a label for the vial 49 and for applying the label to the vial 49. A controller 57C is operably connected to the pill-dispensing module 47, the retriever module 45, a bulk vial handling device 59, and the printer 58 for operating the system.

Space is expensive in retail environments, such as in retail chain stores and local retail drug stores. Typically, pills are stored in bulk in a location well behind a countertop, where the pills are safe from theft, and where there is sufficient room to store the pills in head-high dense-storage cabinets. However, this requires space in the pharmacy area, and further this requires that the pharmacist walk back and forth between customer/patients and the storage cabinets. The present apparatus 40 provides tremendous improvements in reduced space requirements, increased security and density of pill storage, reduce wear on the pharmacist, and improved efficiency and accuracy and timeliness of the operation of filling prescriptions.

The countertop 39 (FIG. 1) includes a work surface 65, side and back panels 66 supporting the work surface 65 at an elbow height, so that the countertop 39 is optimally suited for use by a standing pharmacist sorting and handling pills on its top surface. A front lip 67 may be provided if desired to hold papers and items on the countertop 39. The lip 67 also creates a division from customers/patients, which may be desirable such as for keeping customers/patients from leaning on the countertop 39. The "pharmacist side" of area under the countertop 39 is open. A bump 69 (FIG. 2) may be positioned on a floor surface 70 to engage the wheels 71 of the frame 41 to positively but releasably hold the apparatus 40 under the countertop 39. It is contemplated that a number of different detent arrangements can be used to hold the apparatus 40 under the countertop 39. Notably, it is also contemplated that the present apparatus 40 can be used in locations other than under a countertop, and that the device can be extended vertically to be much higher than waist high. Nonetheless, the optimal arrangement is shown in the figures.

The mobile frame 41 (FIG. 7) includes a pair of inverted T-shaped side frame members 73 connected together by top and bottom beams 74 and 75. Additional components may be attached to the frame 41 for increased rigidity, such as top, side, bottom, and front panels 76, 77, 78, and 79, which enclose a front half of the frame 41. Also, an intermediate panel 79A can be added for increased stiffness, if needed.

However, low weight is potentially important to the apparatus 40 in order to make it semi-easy to move. For this reason, the frame members 73–75 are made of high-strength aluminum extrusions or similar lightweight, high-strength materials. Naturally, a size of the frame 41 also affects the frame requirements.

Figure 7:
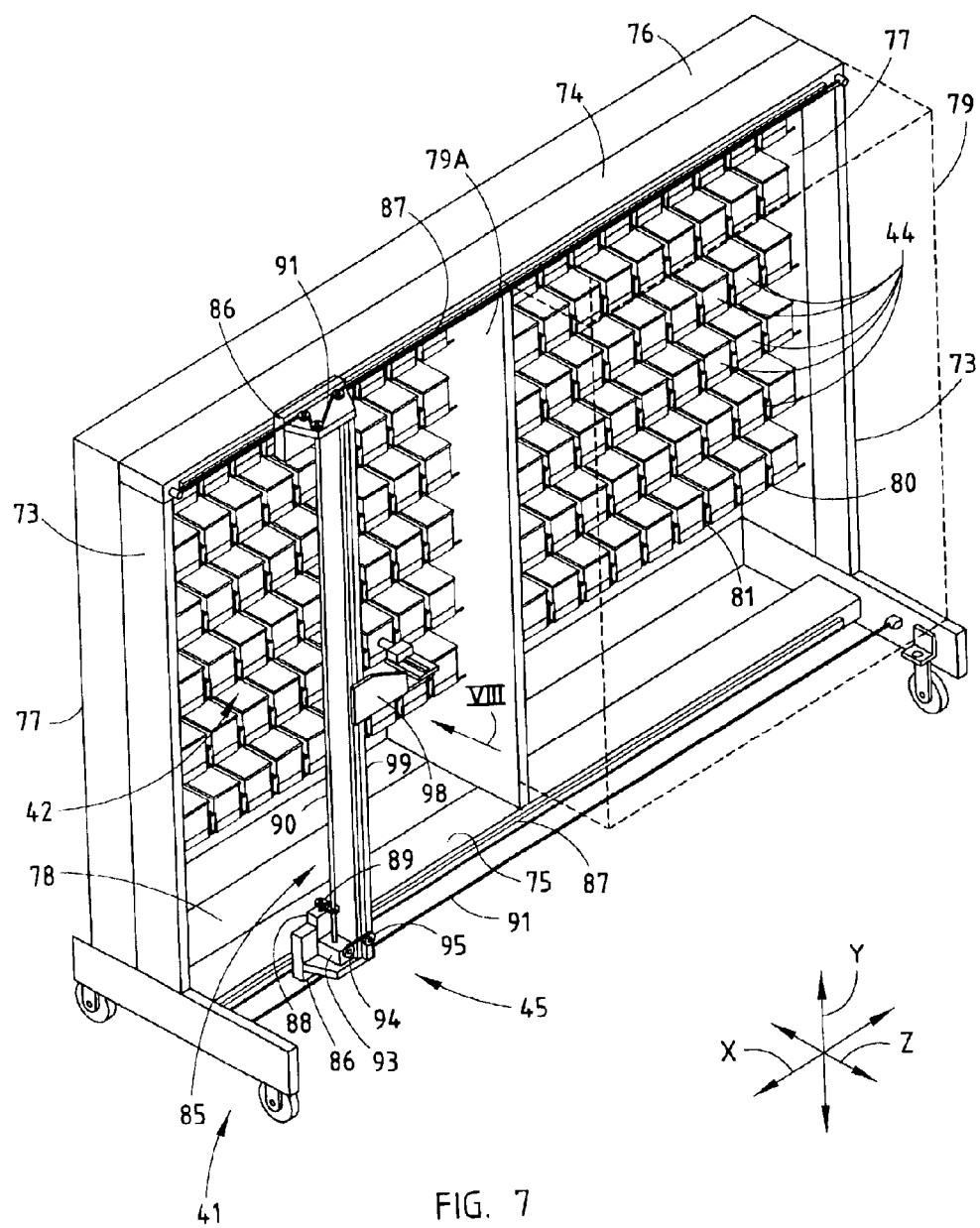
FIG. 7 is a perspective view of the front half of the storage area including storage units stored in the storage area and including the wheeled frame shown in FIG. 2.

A plurality of rods 80 are supported at their ends by side panels 77 and at a middle by an intermediate panel 79A, and L-shaped rod-supporting brackets 81 on the front panel 76 extend forwardly and support a length of the rods 80. A thin shelf panel 82 (FIG. 2) rests on each row of the rods 80 and brackets 81. The rods 80, brackets 81, and shelf panels 82 define a plurality of storage locations shaped to receive the storage units 44. Preferably, the rods 80, brackets 81, and shelf panels 82 are relatively thin to take up a minimum of space. Notably, FIG. 7 illustrates the front array 42. The rear array 43 is removed from FIG. 7, but is shown in the top view of FIG. 4. The illustrated rear array 43 is shown to be smaller than the front array 42, and is six rows high and ten columns wide, while the front array 42 includes six rows high and twenty-two columns wide. This provides one hundred ninety two storage locations for the storage units 44. Nonetheless, it will be clear to a person skilled in this art that the number of rows and columns can be increased to meet specific spacial requirements.

The x-y-z retriever module 45 (FIG. 4) is positioned in the aisle 46, and is operable to retrieve (and replace) any one of the storage units 44 in any the storage locations. It is noted that x-y-z retrievers are available commercially, and that different retrievers can be used successfully in the present apparatus 40, and further that such retrievers can be purchased from a company such as Animatics Company. The illustrated retriever module 45 (FIG. 7) includes a high-rise beam-type frame 85 slidably mounted by top and bottom blocks 86 for horizontal movement in an "x" direction along top and bottom tracks 87 on the horizontal frame members 74 and 75. A servomotor or actuator 88 (or reversible DC motor or reversible step motor or the like) includes top and bottom pulleys 89 connected by a shaft 90. The pulleys 89 engage top and bottom belts 91. The belts 91 extend along the top and bottom tracks 87, and are anchored at each end to side frame members 73. As the motor 89 rotates pulleys 90, the high-rise frame 85 moves horizontally to a selected position, with the top and bottom belts 91 acting together to maintain a vertical orientation of the high-rise frame 85. A second reversible servomotor or actuator 93 is mounted to the bottom block 86 and includes a drive pulley 94. Top and bottom driven pulleys 95 are operably mounted on the high-rise frame 85, and a belt extends between the two driven pulleys 95. The drive pulley 94 is connected to the bottom pulley 95 with a drive belt. A carrier 98 is slidably attached to the high-rise frame 85 for vertical movement in a direction "y" along a track 99 on the high-rise frame 85. When the motor 93 is operated, the carrier is moved vertically to a selected height position.

Figure 8:
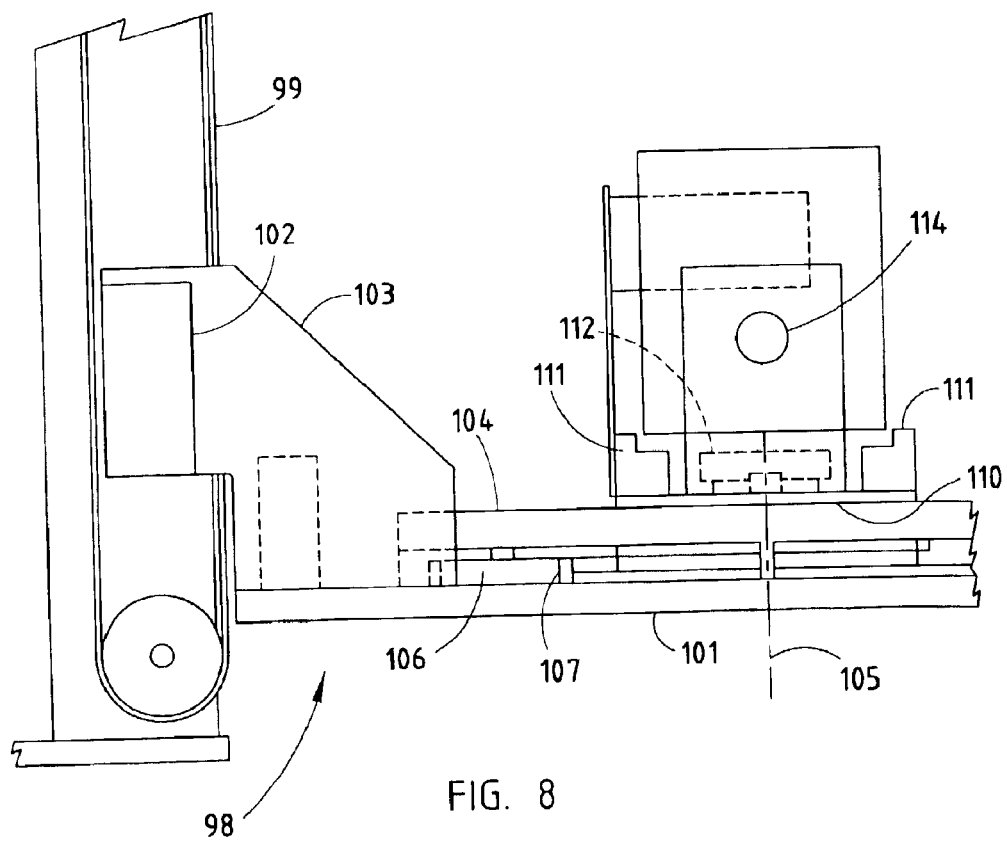

The carrier 98 (FIG. 8) includes a laterally-extending base plate 101 attached to a linear bearing 102 by an "L" bracket 103. The bearing 102 slidably engages the track 99 for providing the vertical movement of the carrier 98 on the high-rise frame 85. The base plate 101 supports a turntable 104 for rotation about a vertical axis 105 (FIG. 9), and a third servomotor or actuator 106 includes a rotatable wheel 107 operably connected to the turntable 104 by a belt 104A so that, upon rotation of the wheel 107, the turntable 104 is rotated to face the retrieving device 108 in front or rear directions (i.e. for grabbing storage units 44 in the front or rear arrays 42 and 43). Edge rollers 105 stabilize the turntable 105A. Attached atop the turntable 104 is an adapter 110 (FIG. 8) that carries a pair of L-shaped tracks 111 and optionally a center magnet 112. The retrieving device 108 includes a fourth servomotor or actuator 113 for extending a rod or slider 114. On the outer end of the slider 114 is an electromagnet 115 (hereafter called the "gripper" or "magnetic coupler") that can be energized to electrically magnetically couple to and attach to a metal washer 116 (FIG. 12A) on the end of the storage unit 44. The slider 114 is extended by rotating actuator 113, which causes a belt 113A that extends around pulley 113B–E to pull the slider along track 113F. When extended, the electromagnet 115 abuts and magnetically attaches to the washer 116 on a selected storage unit 44. The slider 114 is then retracted by the actuator 113, pulling the storage unit 44 onto the tracks 111. The center magnet 112 is optionally energized after the storage unit 44 is fully on the carrier 98 during transport of the storage unit 44 to the pill-dispensing module 47 for increased stability of the storage unit 44 during transport. Micro-switches 118–118C (FIG. 9) are provided on the turntable 104 to assure that the selected storage unit 44 is fully on the tracks 111 (or fully off the tracks 111) before the retriever is allowed to move to another location or to the pill-dispensing module 47.

A database of the location of storage units 44 and their storage location is kept in the memory of the computer 57 and/or the controller 50. Using the computer 57/controller 57C to monitor and sequence the cycle of the modules 88, 93, 106 and 113, along with magnets 112 and 115, different storage units 44 (i.e. different pills) can be selected and transported to the pill-dispensing module 47, as described below.

Figure 6:
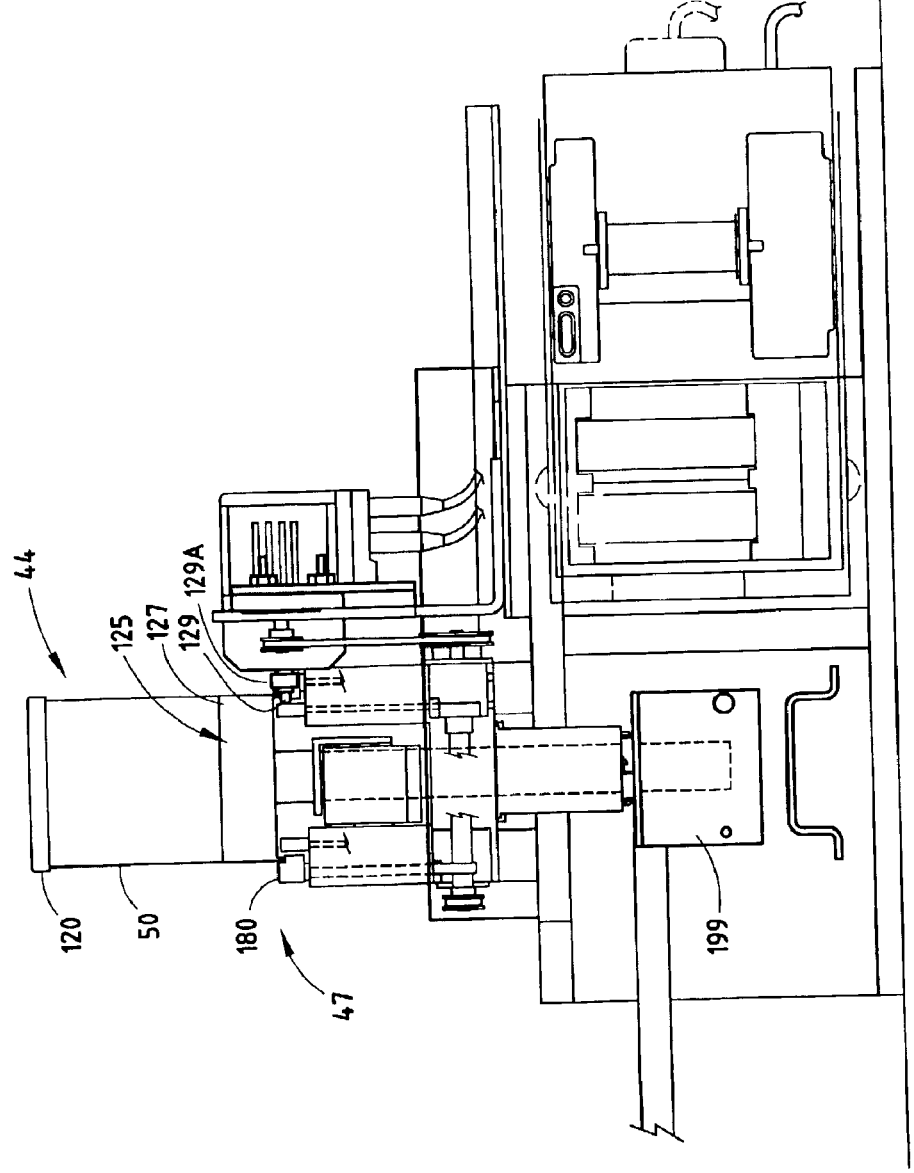
FIG. 6 is an enlarged partial view of a center upper portion of FIG. 3.

The storage units 44 (FIG. 12A) each include a generally rectangular outer container 50, a track 51 positioned in a bottom of the outer container 50, and a hopper 52 movably positioned within the outer container 50 for vertical movement toward and away from the track 51, for reasons described below. The container 50 includes flat side, front, rear and bottom walls forming a box-like shape. A top cover 120 removably snap-attaches to detents 121 along a top edge of the side, front, and rear walls of the container 50. The top cover 120 includes a lip 120A that overlaps the top edge of the container 50 to create a sealed dust-free environment for holding pills in bulk quantities. The container 50 includes a rectangular front opening 122, and a recess 123 on each side with pivot holes 124 therein. A door 125 (also called a "gate" herein) is pivotally attached to pivot holes 124, and includes a flat panel 126 shaped to completely cover the opening 122. The door 125 is spring-biased closed. Side edges 127 of the panel 126 extend slightly outward the recess 123, creating an exposed tab that can be engaged by an offset actuator pin 129 on a servo-motor or actuator 129A (FIG. 6) at the pill-dispensing module 47 for opening the door 125 to allow pills 48 to drop from the track 51 out of the container 50.

An important aspect of the door 125 is that, when the door 125 is in a near-closed position, the flat panel 126 swings in a direction 127A substantially parallel the groove in the track 51. This causes any pills 48 that are hanging on an edge of the track 51, ones which are ready to fall but that have not yet quite fallen, to be pushed back onto the track 51. This avoids many of the problems in the prior art caused by pills hanging on an edge of their tracks or pill feeding system. Specifically, in the prior art, these "hanging" pills often drop after the operation of counting pills has stopped (resulting in "extra" pills being dispensed, and, in effect, given away for free). Alternatively, these "hanging" pills potentially could drop as the bulk storage unit is being transported away, or get caught in a door such that they hold the door partially open. Further, some doors may crush the "hanging" pills, causing debris problems, sanitation or cross-mixing problems, and other related problems. The present apparatus solves this problem by pushing any "hanging" pills back onto the track 51, so that the "hanging" pill is held within the container 50 in a sanitary and sealed environment. In the fully closed position, the flat panel 126 fits into notches 128 in the side walls so that it aligns with the front wall of the container 50.

The bottom of the container 50 (FIG. 15) further includes two large holes 130 that align with the magnets on the vibrator 53, as described below. The bottom also includes four smaller holes 131 aligned with the stand-off legs 132 on the hopper 52, for reasons also described below.

The hopper 52 (FIG. 12A) is shaped to fit slidably within the container 50. Specifically, the hopper 52 includes an upper portion with flat side, front, and rear walls 134–137 forming a rectangular ring shape that fits closely within the walls of container 50. The close fit prevents pills from slipping between the walls of the hopper 52 and the walls of the container 50, but allows friction-free vertical sliding movement of the hopper 52 within the container 50. The lower portion of the hopper 52 includes inwardly angled side, front, and rear walls 138–141. The angled walls 138–141 define an opening 142 at their lower end. The angle of the angle rear wall 141 is greater than the other walls 138–140, such that the opening 142 is located at an upstream end of the track 51. Two stand-off legs 132 extend downwardly from each of the angled side walls 138 at locations aligned with the small holes 131 in the bottom of the container 50. The ends of the legs 132 are chamfered so that they extend partially into the small holes 131, but the legs 132 are of sufficient diameter so that the legs 132 do not fit through the holes 131. Notably, the hopper 52 "floats" within the container 50, which reduces the magnitude and sharpness of vibratory forces on pills 48. This is very beneficial because less damage, dust, and debris result from handling pills 48, thus maintaining a cleaner environment.

Figure 17A:
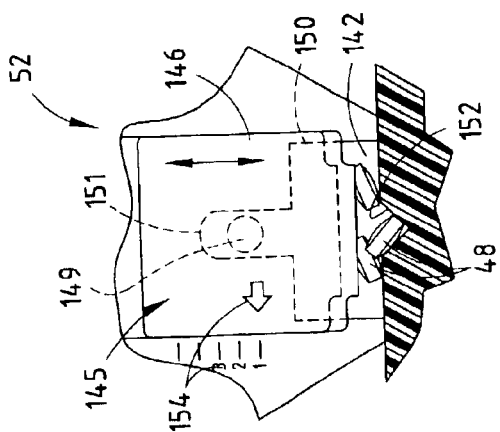
FIG. 17A is an enlarged fragmentary view of the gated opening of the hopper shown in FIG. 12A.
Figure 19A:
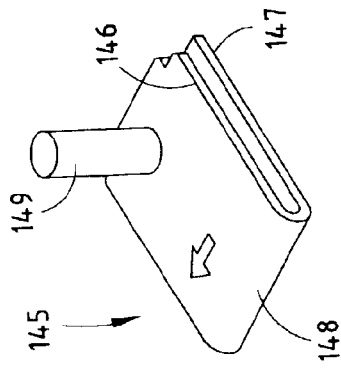
FIGS. 19–19A are perspective and side views of the adjustable gate component shown in FIG. 17A.
Figure 17:
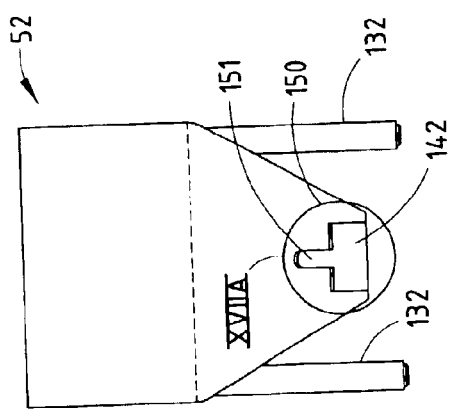
FIGS. 16–18 are side, front, and top views of the internal hopper shown in FIG. 12A.
Figure 19:
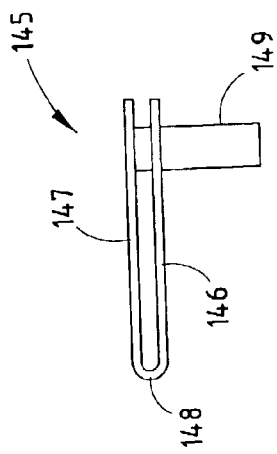
Figure 16:
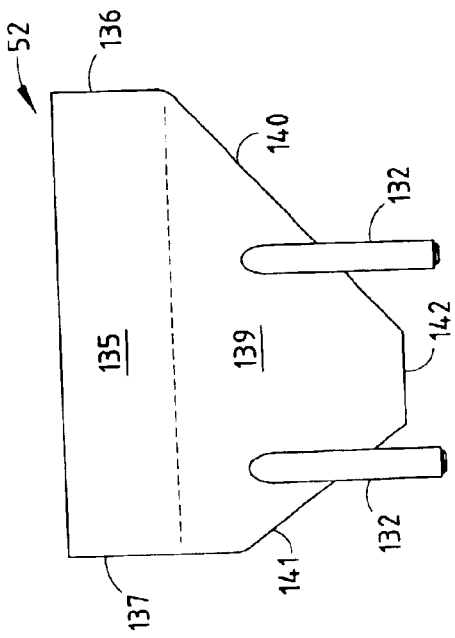
Figure 18:
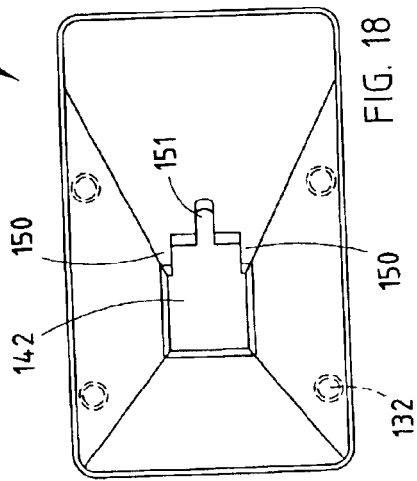
Figure 20A:
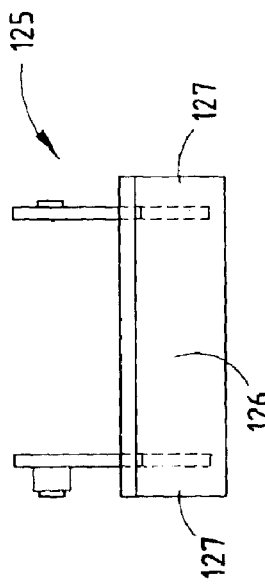
FIGS. 20–20A are side and front views of the door shown in FIG. 12A.
Figure 22:
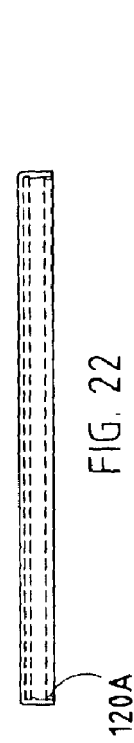
FIGS. 21–22 are top and side views of the top cover shown in FIG. 12A.
Figure 20:
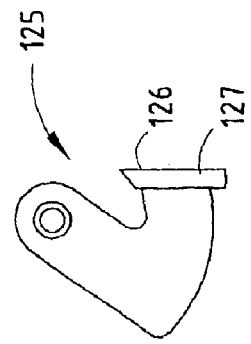
Figure 21:
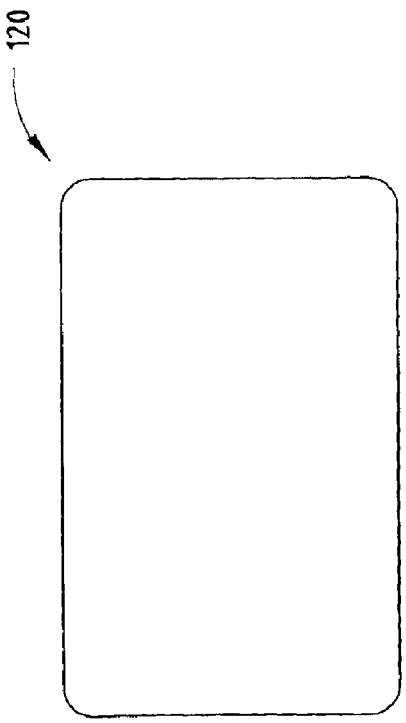

An adjustable gate 145 (FIGS. 19–20) includes a opposing tabs 146 and 147 attached together by a bend 148, and further includes a perpendicular pin 149 that extends through the tabs 146 and 147. The tabs 146 and 147 frictionally but slidably engage the marginal material 150 on the angled wall 141 that defines the opening 142. The pin 149 also engages a slot 151 that is also defined by the marginal material 150. The pin 149 stabilizes the gate 145 by engaging slot 151, and also it acts as a handle to facilitate adjustment of the gate 145. The gate 145 is adjustable toward and/or away from the track 51, to increase or decrease a size of the opening 142. Notably, perhaps more important than the size of the opening 142, is a size of the gap 152 under the gate 145 to the track 51. The gap 152 can best be seen in FIG. 17A. Notably, pills 48 pill up in the "upstream" end of the track 51 below the opening 142 and behind the gate 145, and the pills 48 must travel under the gate 145 (i.e. through the gap 152) as the pills 48 travel along the track toward the drop point at the downstream end of the track 51. As shown by FIG. 17A, considerably more pills 48 will travel through the gap 152 and under the gate 145 when the gate is adjusted upwardly.

It is noted that in some prior art systems, separate pieces defining different sizes and shapes of "gaps" were sold by factories, in order to optimize pill-dispensing systems. However, this resulted in a myriad of additional special-order custom-built parts and pieces. While this may be beneficial to the manufacturer of the pill-dispensing equipment due to increased reordering of specialty parts and pieces, it caused a major problem for users, since the users "never" seemed to have the right mix of parts that they needed. As a result, they continually had to order new and different parts and pieces from the manufacturer, and it added considerably to cost and maintenance problems. The present adjustable gate 145 is very simple and easy to adjust, simple to use, intuitively logical in its adjustment and flexibility of use, and easy to replace. Further, it uses a single adjustable gate and simple attachment mechanism. By placing indicia 154 (FIG. 17A) along the slot 151, the factory can still suggest optimal gate settings and gap sizes for particular drugs. Thus, recommended initial settings can be quickly and easily made.

Figure 32:
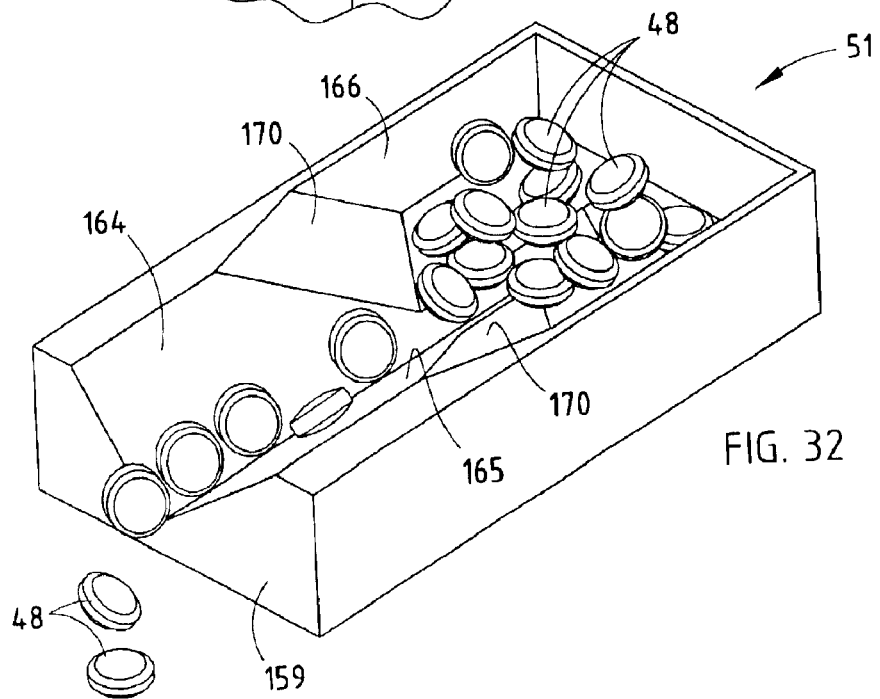
FIG. 32 is a perspective view showing pills positioned on the track and bunched up at the transition area where the pills are redistributed on the track to help distribution and singulation of the pills.

As noted above, the track 51 (FIGS. 10–12A) is adapted to be positioned on a bottom of the outer container 50. The track 51 (FIG. 23) is designed to be useful for feeding solid pills 48 along its length upon vibration of the track 51. The track 51 is made of a solid polymeric block member 155 having a top surface 156 defining a generally horizontal plane. The side surfaces 157 of the block member 155 are shaped to fit between the stand-off legs 132, with a rear wall 158 resting adjacent the rear wall of the container 50, and a front edge 159 positioned under the front wall of the container 50 and close to but inside the door 125. A groove 160 is formed in the block member 155 that extends from an upstream end 161 of the solid member 155 across a middle section 162 of the solid member 155 to a downstream end 163 of the solid member 155. The groove 160 further extends to the front edge 159 of the solid member 155 at the downstream end 163. The groove 160 in the downstream end 163 (FIG. 26A) defines a well-defined "V" shape with first angled side surfaces 164 and 165 that extends at about 45 degrees to vertical, and that are adapted to convey singulated pills 48 (FIG. 32) to and off the front edge 159 one at a time. (See FIG. 32.) The groove 160 in the upstream end 161 (FIG. 26C) defines an enlarged pocket with angled side surfaces 166 and a flat bottom 167 shaped to store pills. The pocket in the upstream end 161 is inclined toward the downstream end 163, and includes a small "V" groove 168 that leads to and is aligned with a bottom of the larger "V" groove 160, such that it is shaped to slidingly convey pills 48 dropped out of the hopper 52 onto the upstream end 161 toward a center of the upstream end 161 and into the small groove 168. The portion of the groove 160 in the middle section 162 is formed from compound-angled side surfaces 170 that are diamond shaped (in top view, see FIG. 26). The angled surfaces 170 extend at a vertical angle greater than 45 degrees (compare FIG. 26B to FIG. 26A) and extend at compound angles to the first and second angled side surfaces 164–166 to form a transition pocket. The transition pocket acts as a "speed bump" to redistribute bunched-up pills 48 as the bunched-up pills 48 travel from the upstream end 161 into the middle section 162. By this arrangement, the transition pocket unbunches and breaks up bridging of the pills 48, and redistributes the pills 48. It is contemplated that a second "speed bump" may be included along groove 160 if a second redistribution of pills would help singulation. The surfaces 166 then center and singulate the pills 48 as the redistributed pills 48 travel out of the transition pocket in the middle section 162 toward the downstream end 163. It is noted that the groove 160 in the downstream end 163 is shaped to handle a variety of different shaped pills 48. In the illustrated arrangement, the pills 48 are disk-shaped, and can roll along either surface 164 or 165 (see FIG. 32), with their flat side resting on the other surface 164 or 165. Long pills are travel well along this groove 160, and bridging is broken up in an efficient manner, based on preliminary testing.

A bottom of the track 51 (FIG. 27) includes a pair of magnetically responsive metal pieces, such as iron or steel washers 171, that can be magnetically gripped by a magnet(s). Preferably, the washers 171 are inset into a bottom of the track 51 so that the track 51 provides a smooth flat bottom surface. One washer 171 is near a front end of the track 51, and the other washer 171 is near a rear end, which allows the vibration nodes 185 and 186 to provide an unbalanced vibration on the front or rear of the pill track 51.

The pill-dispensing module 47 (FIG. 33) is provided for unloading pills 48 into a vial 49. The pill-dispensing module 47 includes a docking station for receiving a selected storage unit 44, a pill counter 54 for counting pills 48 dispensed from the storage unit 44, and a lift 55 for lifting the hopper 52 to break bunched-up pills 48 during the pill-dispensing cycle. More specifically, the pill-dispensing module 47 includes a base plate 175, and a raised platform plate 176 spaced above the base plate 175, both mounted to the frame 41. For example, the base plate 175 can be mounted to the side frame member 73 and an intermediate vertical panel 79A (FIG. 7) at an intermediate height between the top and bottom beams 74 and 75. A docking station is formed on the platform 176 and includes a pair of spaced-apart stands 178 and 179. A pair of "L" tracks 180 and 181 (identical to the tracks 111 on the x-y-z retriever 45) are positioned on the stands 178 and 179. However, tracks 180 and 181 are fixed to vertical rods 182, which in turn are slidably mounted to the stands 178 and 179. An axle 183 extends through the stands 178 and 179, and an internal cam (not specifically shown) on the axle 183 is configured to raise and lower the tracks 180 and 181 as the axle 183 is turned. A pulley 184 on the end of the axle 183 is operably connected to an actuator or servomotor 185 for controlled rotation so that a height of the tracks 180 and 181 can be closely controlled. In their raised position, the tracks 180 and 181 align with the tracks 111 on the carrier 98 of the retriever 45. This allows the slider 114 to move a selected storage unit 44 from the tracks 111 onto the tracks 180 and 181.

Figure 28:
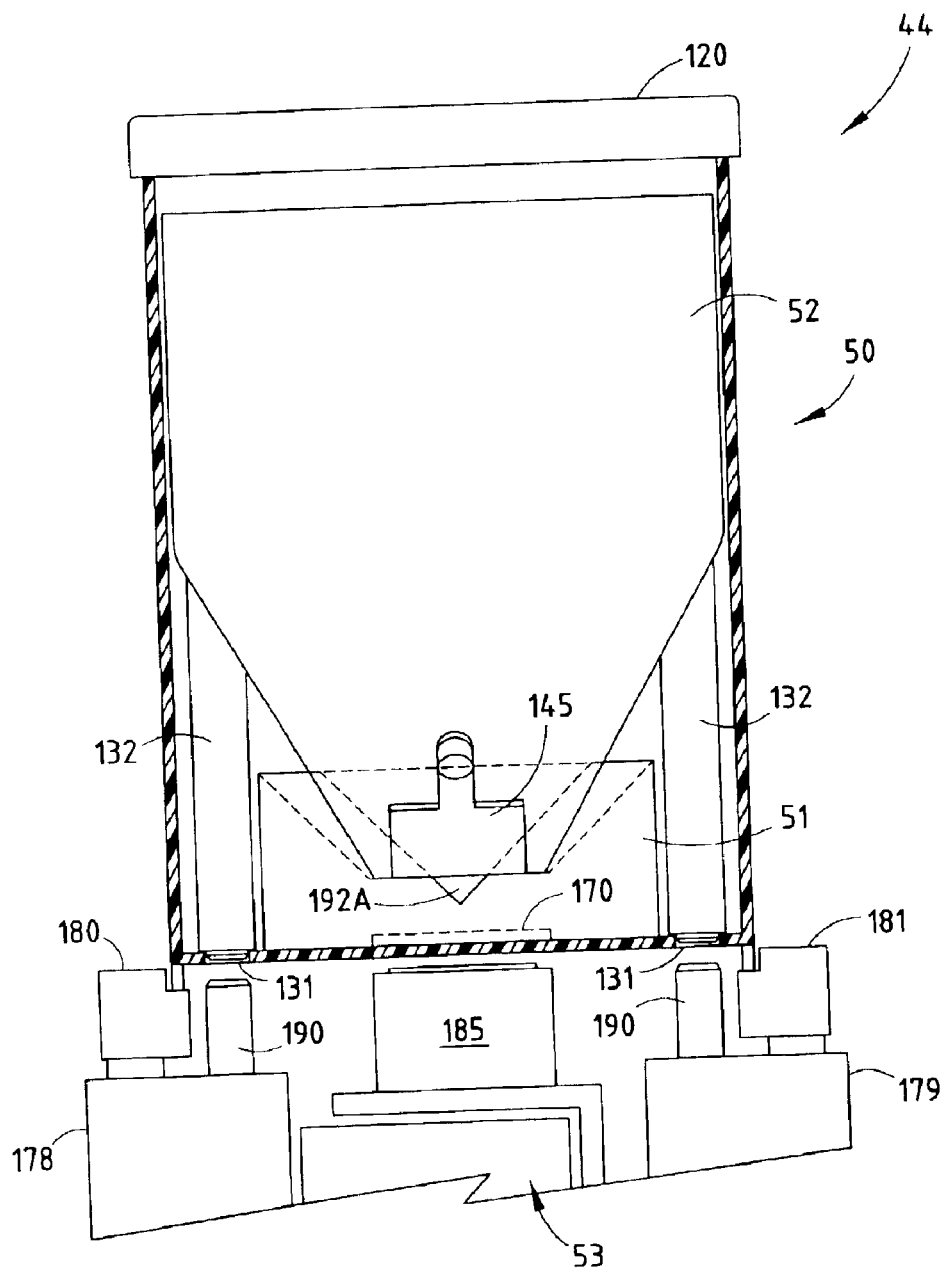
FIG. 28 is a front view, partially in section, showing a position of the outer container and inner hopper during loading of the storage unit onto the pill-dispensing module.
Figure 29:
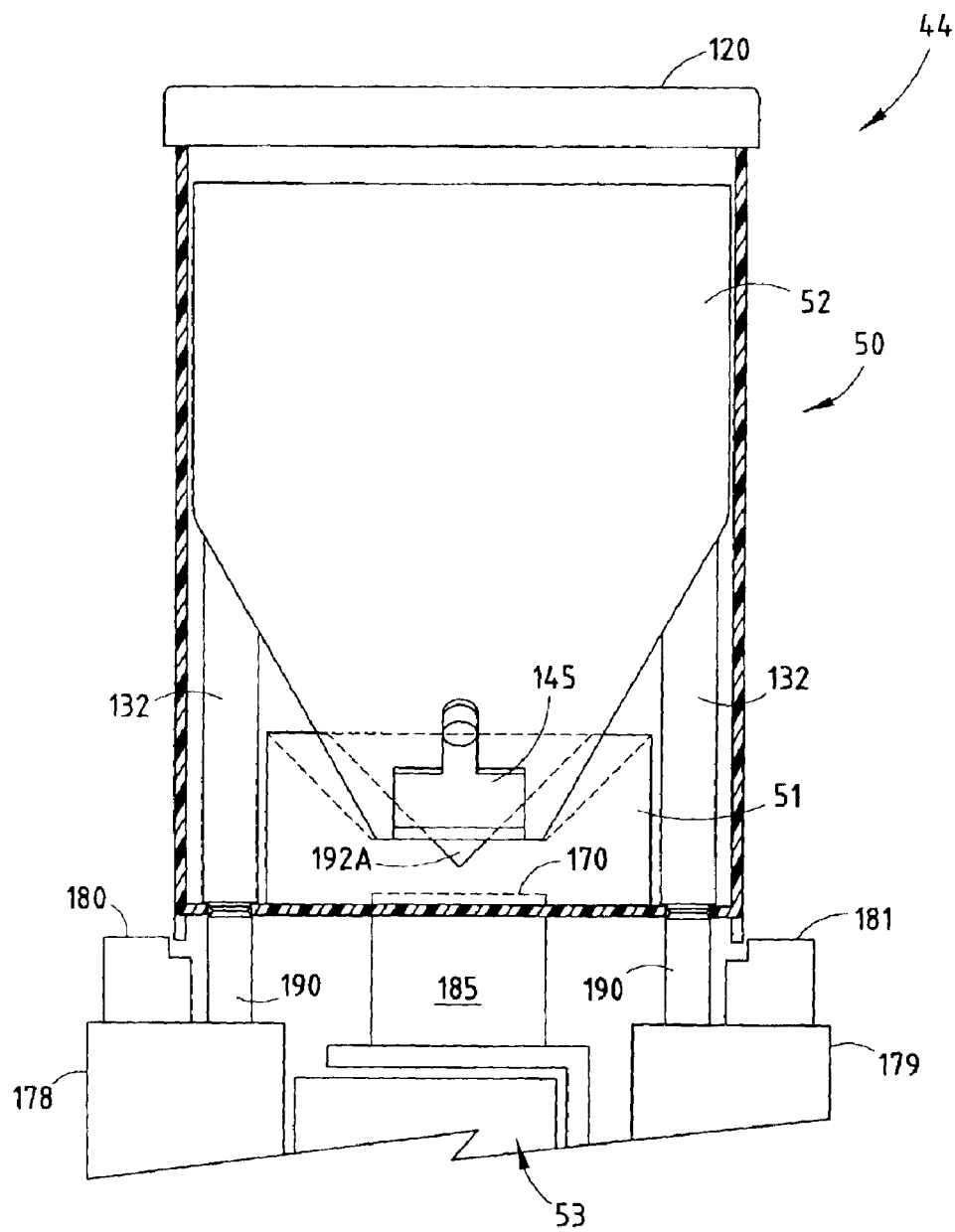
FIGS. 29–30 are similar to FIG. 28, but FIG. 29 shows the internal hopper lowered for starting a pill-dispensing sequence, with the gate being in a very restrictive small-gap position.

The vibrator device 53 (also called an "oscillator") is positioned between the tracks 180 and 181, and includes front and rear up-protruding vibratory nodes 185 and 186. The nodes 185 and 186 are positioned low enough such that the bottom wall of the container 50 slides over them when a selected storage unit 44 is being loaded into the docking station (i.e. when the tracks 180 and 181 are in the raised position—see FIG. 28). When the tracks 180 and 181 are lowered (see FIG. 29), the vibratory nodes 185 and 186 extend through the holes 130 in the bottom wall of the container 50 and touch and then magnetically couple to the washers 170 and 171 on a bottom of the pill track 51. This allows the vibratory device 53 to vibrate the pill track 51 without violating or contaminating the internal space within the container 50. By selectively vibrating one or both of the nodes 185 and/or 186, the flow of pills 48 along the pill track 51 can be closely controlled. The direction and amplitude of vibration of each node can be varied or controlled for optimal operation. For example, the front node 185 can be vibrated at about 7°, and the rear node 186 can be vibrated at about 10° from vertical.

Figure 30:
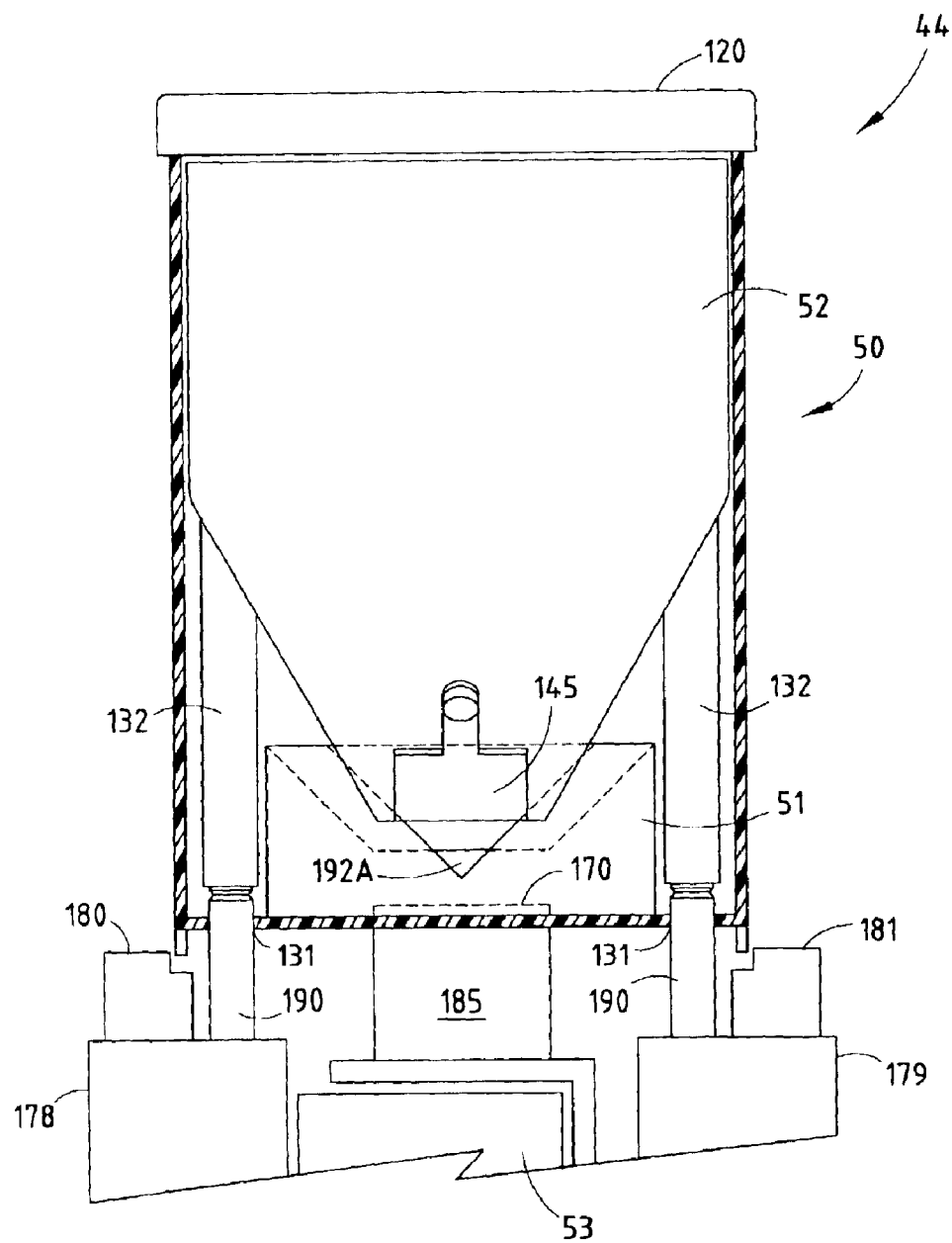
Figure 31:
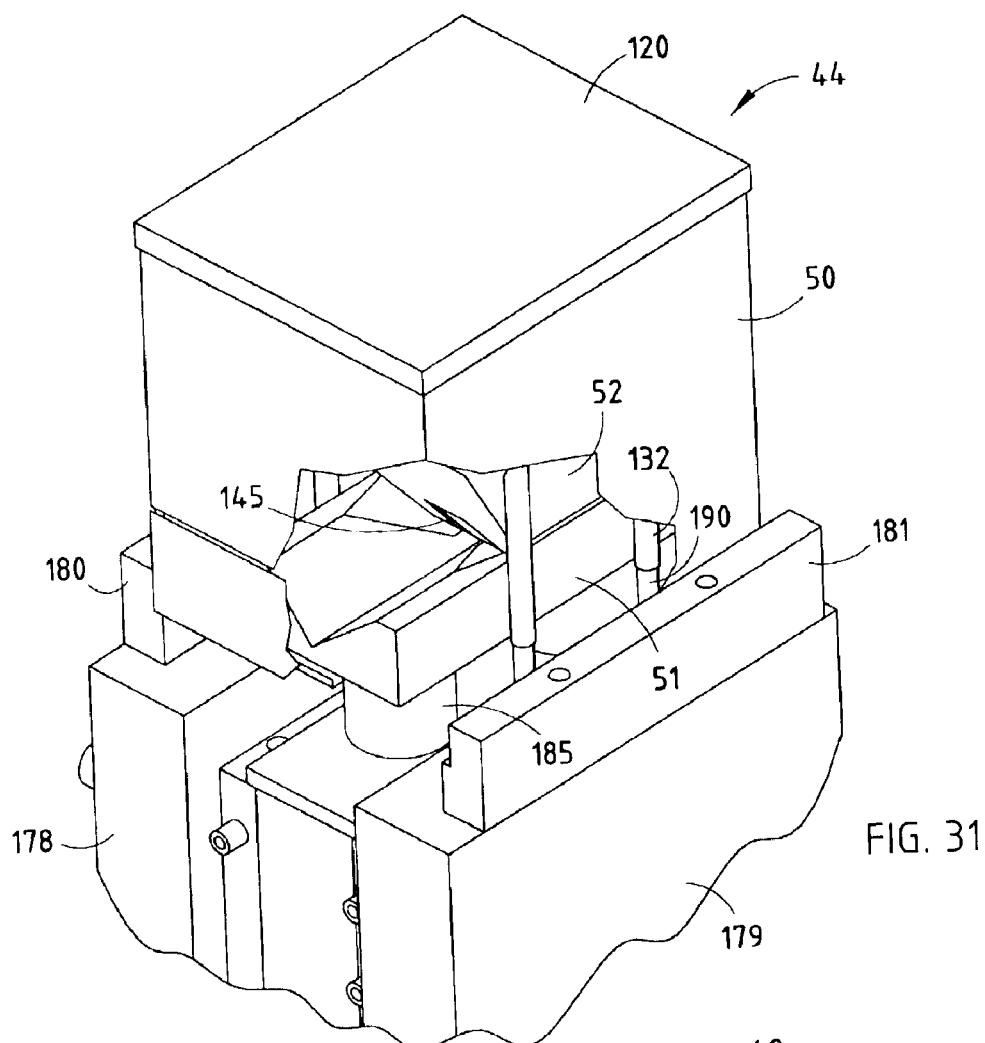
FIG. 31 is a perspective view, with the container partially broken away, to show the track and internal hopper ready to drop pills in the pill-dispensing module.

The lift 55 (FIG. 30) includes upright lift pins 190 that extend vertically through the stands 178 and 179. A second axle extends through the stands 178 and 179 parallel the axle 183 and is operated by a second actuator much like the axle 183. Specifically, the lift 55 includes a cam on the second axle that, when rotated, causes the pins 190 to telescopingly extend. When the lift pins 190 are lifted/extended, they extend through the holes 131 in the bottom wall of the container 50 and up against the ends of the stand-off legs 132, such that they cause the hopper 52 to raise within the container 50. (See FIG. 30, and compare FIG. 30 to FIG. 29. Also, compare the enlarged V-shaped gap 192 in FIG. 30 with the smaller gap shown in FIG. 29.) It is noted that the slider 114 can also be operated to help motivate pills 48 along the pill track 51.

In the pill-dispensing module 47 (FIG. 33) pills 48 that drop off the front edge 159 of the pill track 51 fall through a funnel 195, through an optical pill counter 54, through a second funnel 197 into a vial 49 held in a vial holding station or nest 199. Optical pill counters, such as the pill counter 54, are well known in the art such that a detailed description of them is not required. The illustrated counter 54 is attached in an aperture in the platform 176 in front of the stands 178 and 179. A roll of sticky labels 200 is routed through a printer 58 and into an applicator 58A. The applicator 58A pulls off the releasable paper from the sticky side of the label 200, and threads the printed label 201 toward that side surface of a rotating vial 49. The vial 49 is rotated by a spinner motor or actuator 203 that spins a roller 202 rotatably engaging the side surface of the vial 49. The roller 202 presses the printed label 201 into adhering contact with the side surface. A bar code reader 205 reads a bar code on the printed label 201 and a second bar code reader 205A reads a second bar code on the container 50 to assure that the correct pills 48 are being put into the vial 49.

Vial handling devices 59 are well known in the art such that a detailed description is not required. Accordingly, the discussion below is sufficient for an understanding of the present inventive concepts by persons skilled in the art.

Figure 5:
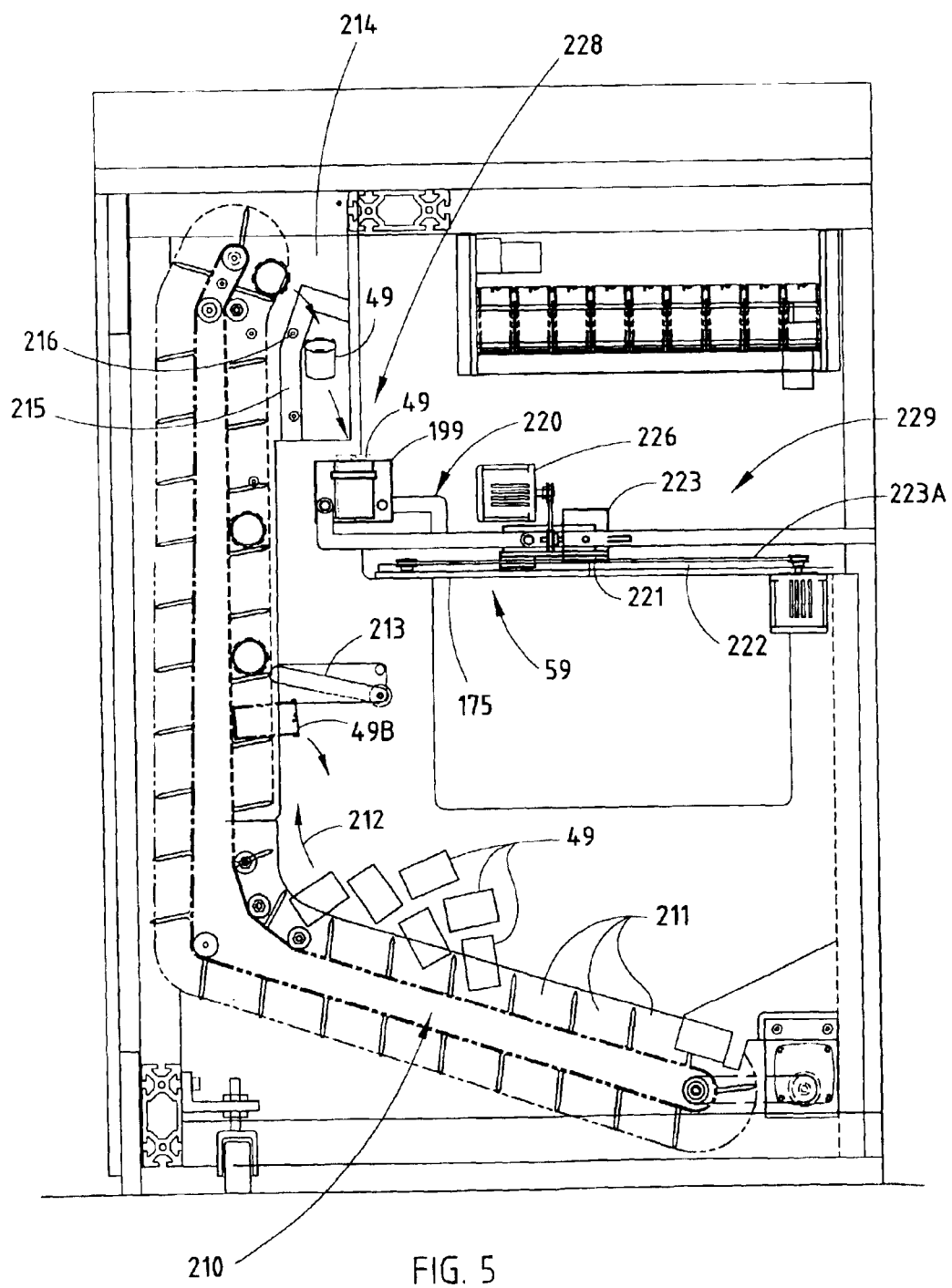
FIG. 5 is an enlarged partial view of the left-hand portion of FIG. 3.
Figure 34:
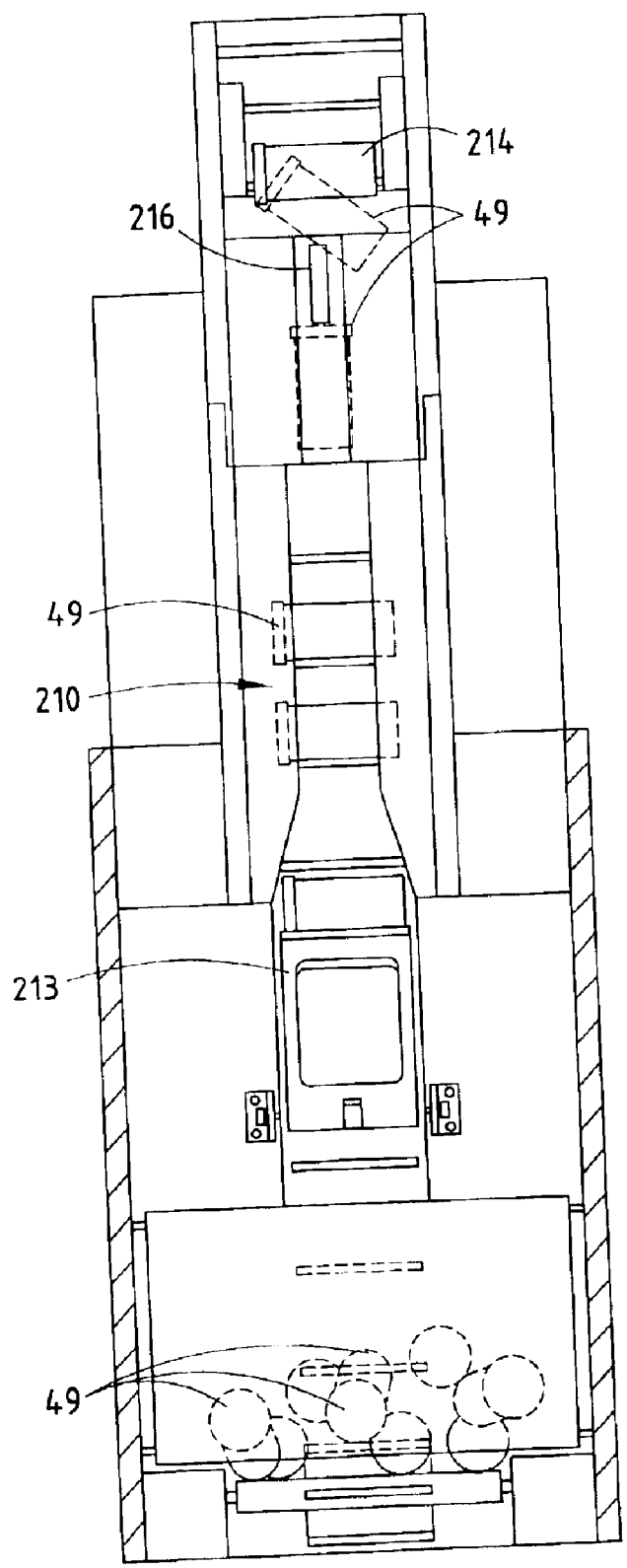
FIG. 34 is a side view of the vial bulk-handling apparatus.

The vial-handling device 59 (FIG. 5) includes a conveyor 210 with nests 211 shaped to hold vials 49. The conveyor 210 is motivated along the direction 212. Vials such as vial 49B that do not seat fully into the nests 211 are knocked off the conveyor 210 by a flapper 213. Vials 49 that successfully seat and are conveyed to a top of the conveyor 210 are unloaded at a vial loading station 214. The vial loading station 214 includes a tipper 215 that tips the vial 49 upright, so that the bottom of the vial 49 is down and the open end of the vial 49 is up. Different tippers are known in the art. The present tipper 215 includes a center protrusion or ridge 216 (FIG. 34) that engages a center of the vials 49 as they are bumped off the conveyor 210. The bottom of the vial 49 is heavier (since the top of the vials are open), such that the bottom naturally swings downwardly ahead of the top when the protrusion 216 drags on a side of the vial 49. Thus, the vial 49 is oriented as the vial 49 further drops into a cylindrical nest 199 (FIG. 5) of the vial handler module 220.

Figure 3:
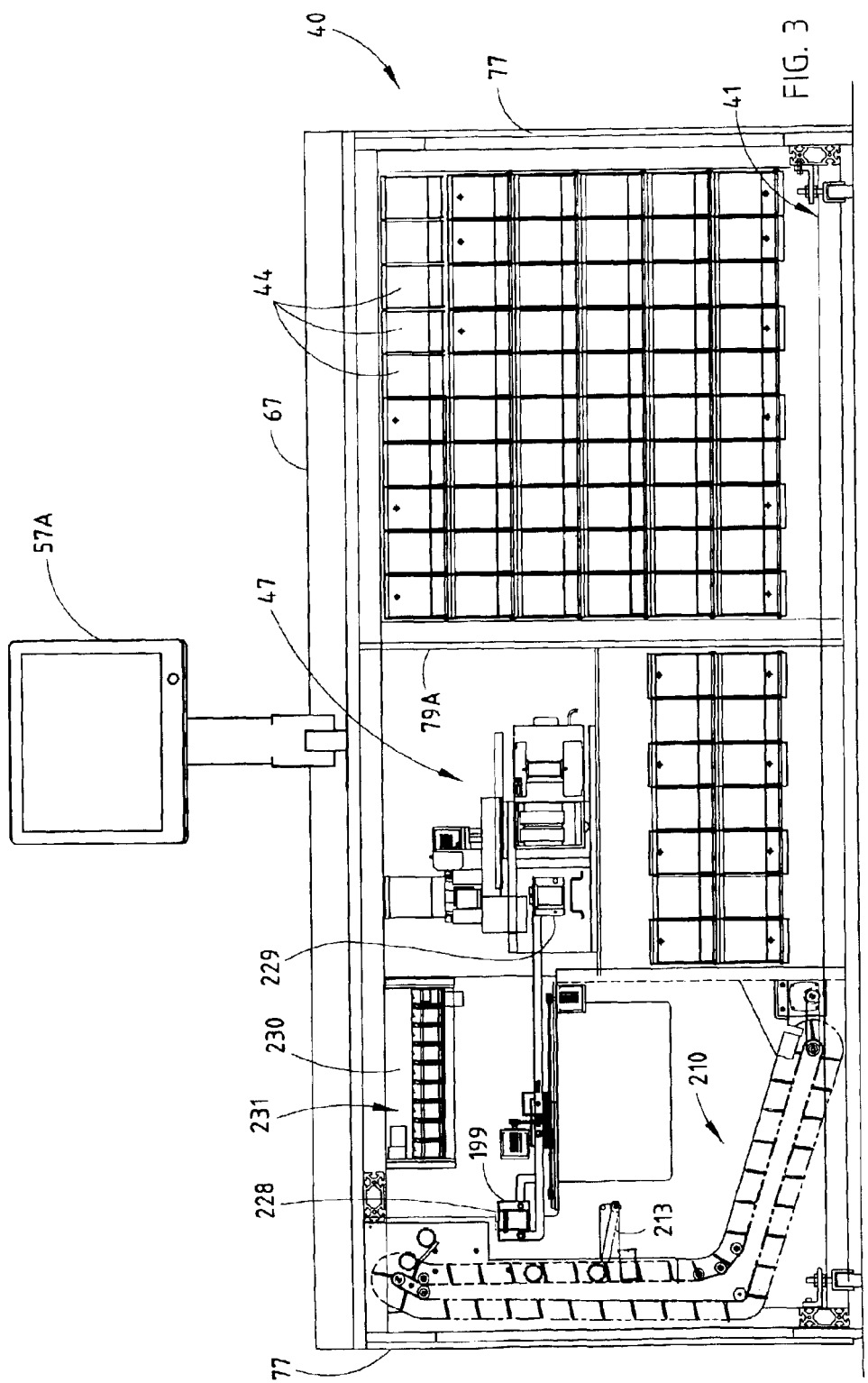
Figure 35:
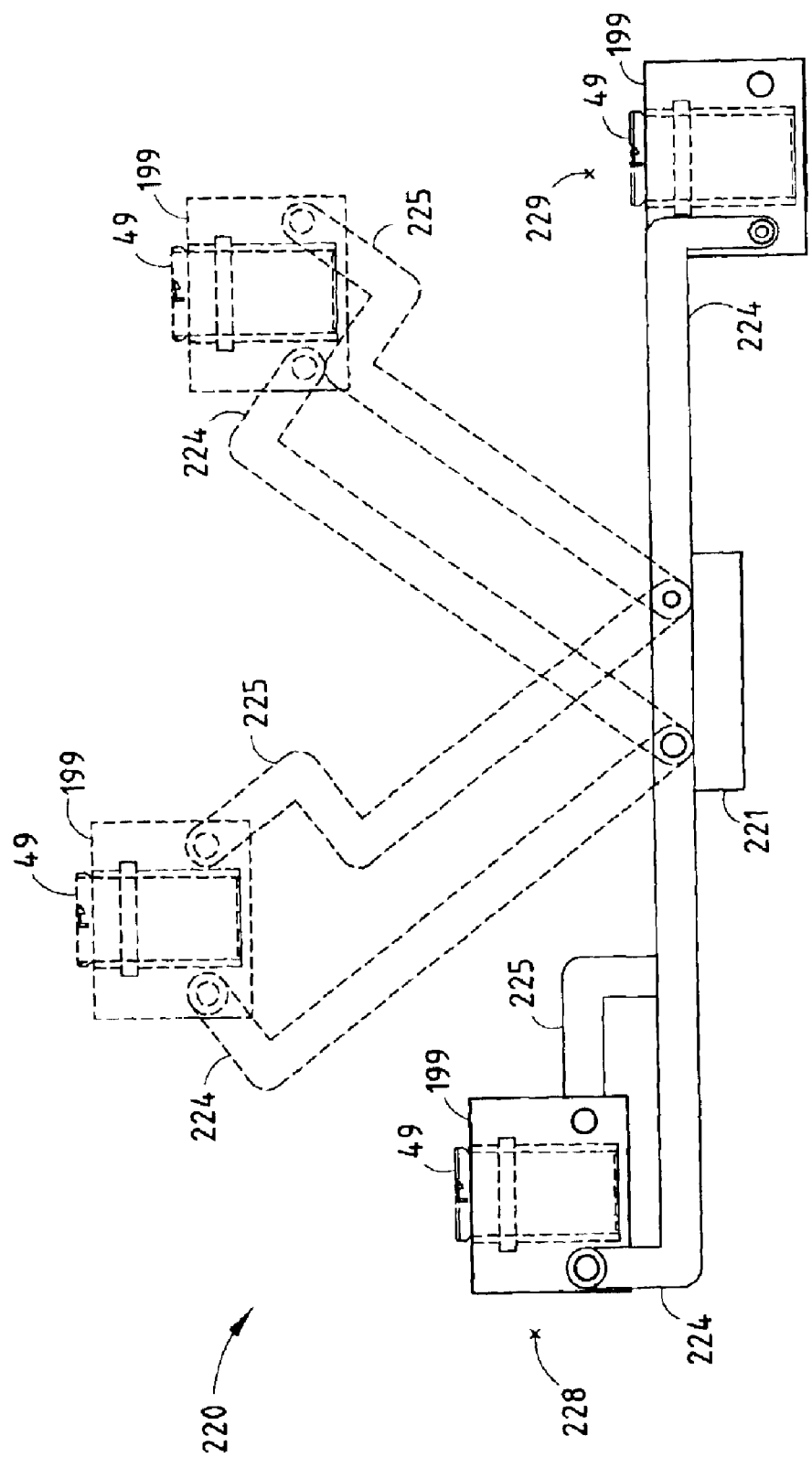
FIG. 35 is a side view showing different positions of the vial handler.

The vial handler module 220 (FIG. 5) includes a base slider 221 slidably mounted on a linear track 222 for lateral movement in the "x" direction previously defined. The track 222 is supported on the base plate 175 (or on another stationary mounting plate on the frame 41), and actuators 223 are operably mounted to the base plate 175 and are coupled to a band 223A for moving the base slider 221 along the track 222. The vial holder 119 (FIG. 35) is mounted to the base slider 221 by two pairs of arms 224 and 225 that work in a parallelogram arrangement to always keep the vial holder 218 level and facing upwardly. A second actuator 226 (FIG. 5) is operably attached to the arms 224 and 225 for pivoting them on the base slider 221 from a left position to a right position. Operation of the second actuator 226 causes the arms 224 and 225 to move the vial holder 218 from a raised left-hand position at location 228 for catching vials 49 as they come off the conveyor 210, upwardly overcenter through an arc to a lowered right-hand position 229 for positioning vials 49 in the pill-dispensing module. (See FIG. 3.) After the vial 49 is labeled and the pills 48 loaded into the vial 49, the actuators 223 and 226 combine to position the vial 49 at a selected height and lateral position suitable for depositing the vial 49 in one of the channels 230 (FIG. 3) of the filled-vial holding station 231. It is contemplated that all of the filled vials 49 for a particular patient will be unloaded in a single channel 230. Thus, all of the prescriptions will be in one ready location, making it easy for the pharmacist to give the patient all of their prescriptions. The vials 49 can be unloaded from the vial holder 218 into one of the channels 230 by different means. For example, the vial holder 218 can include a release or actuator that motivates the vials 49 out of the vial holder 218. Alternatively, the filled-vial holding station 231 can include projecting fingers that extend to grip a filled vial 49 in the vial holding station 231 to push the filled vial 49 into a selected channel 230.

The prescription information station 56 (FIG. 2) includes a computer 57 with a database for receiving and storing patient prescription information, the printer 58 (FIG. 33) for printing a label for the vial 49 and for applying the label to the vial 49, the screen or monitor 57A (FIG. 2), the keyboard 57B, and other items as required to input, retrieve, and view patient information. The controller 57C (FIG. 33), which includes the computer 57, is operably connected to the components of the pill-dispensing module 47, the retriever module 45, a bulk vial handling device 59, and the printer 58 to control all systems of apparatus 40. It is noted that the computer 57 could be a laptop computer or other separate computer unit, but that it does not need to be a separate stand-alone unit. Instead, it is contemplated that an electronic center could be constructed within the apparatus 40, such as near the pill-dispensing module, that includes computer cards, motherboards, and the like for controlling the apparatus 40.

The present apparatus 40 is highly modular, and takes maximum advantage of off-the-shelf units that can be purchased and used in the apparatus 40 by attachment to the frame 41. By this arrangement, many different options can be added or deleted, based on a pharmacist's preference, or based on a storeowner's preference, or based on customer preferences. For example, the computer can be purchased from Dell Computer; the flat screen HMI can be purchased from Christianson Displays; and the bearing can be purchased from Roll-On.

Figure 36:
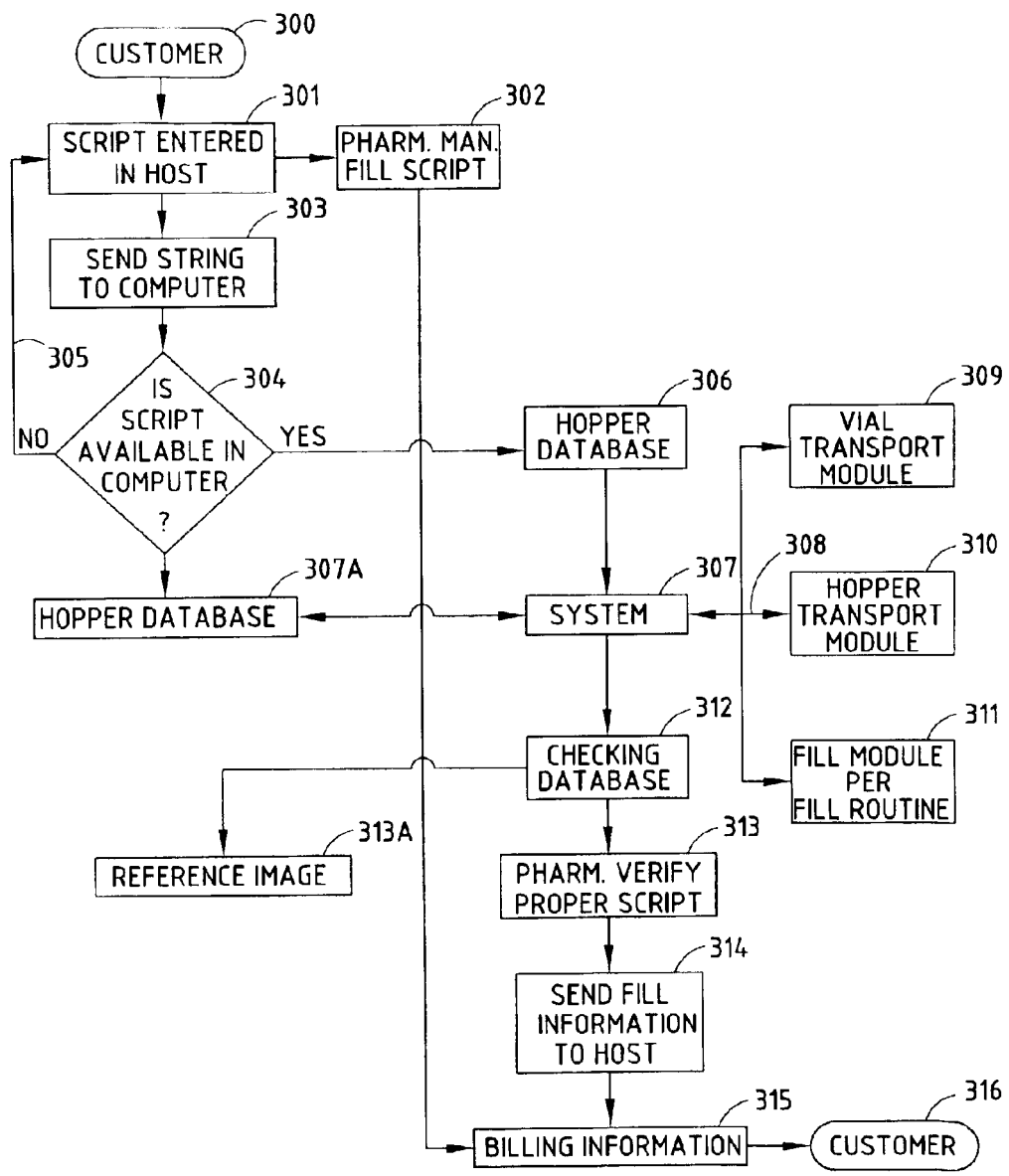
FIGS. 36–38 are flow charts showing the method of script filling, the method of filling vials at the pill-dispensing module, and the method of restocking the storage units.
Figure 37A:
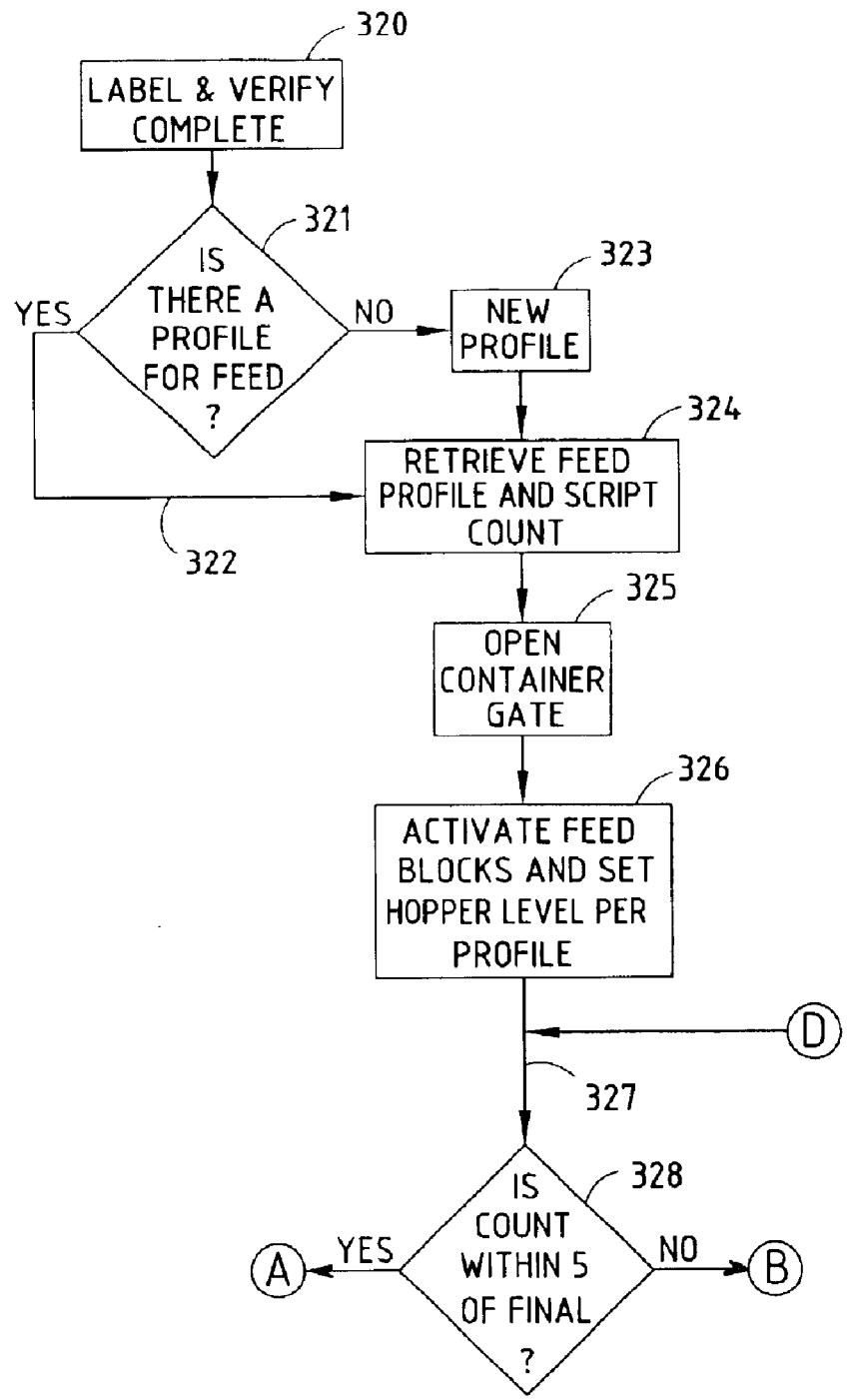
Figure 37B:
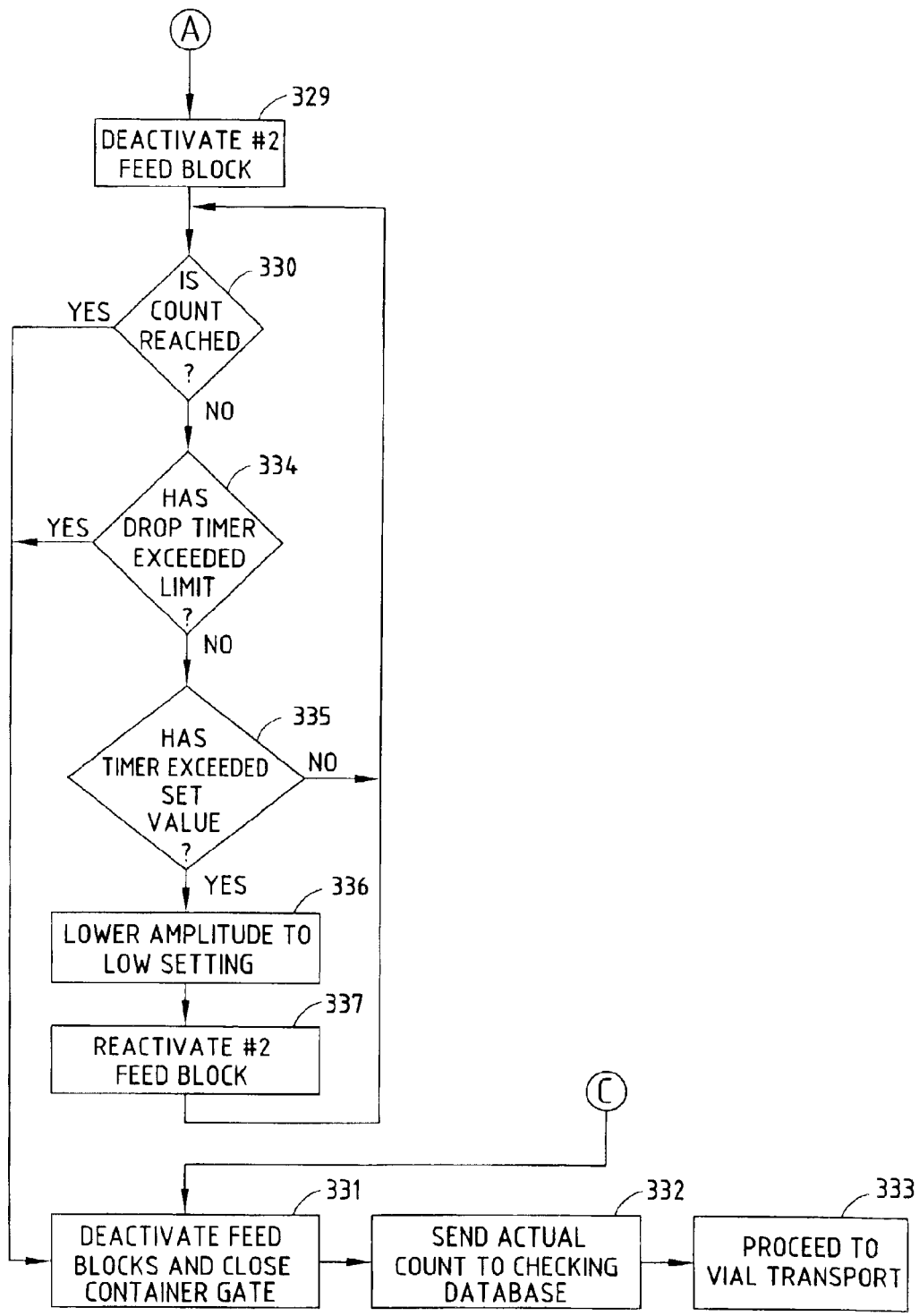
Figure 37C:
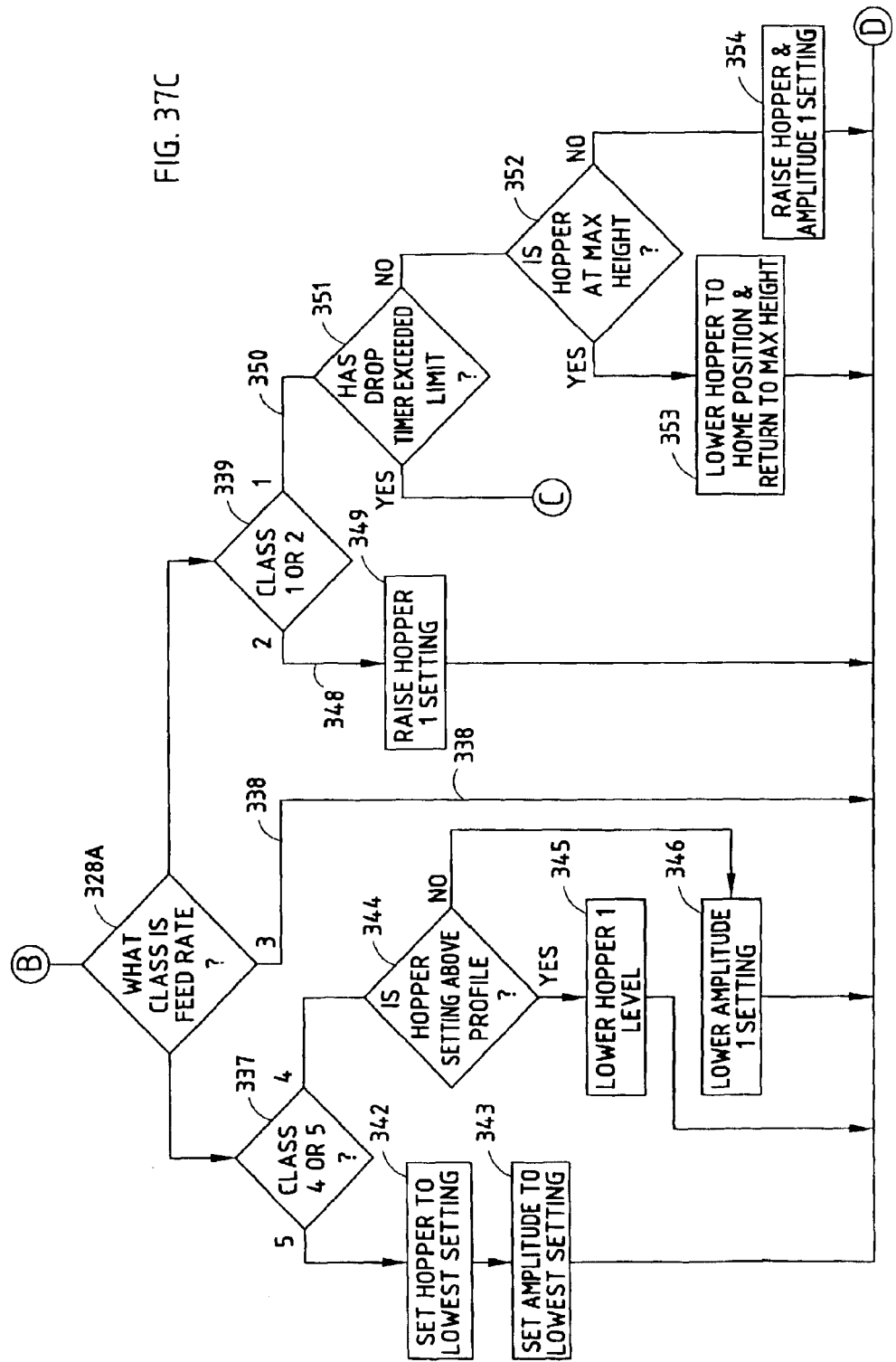
Figure 38:
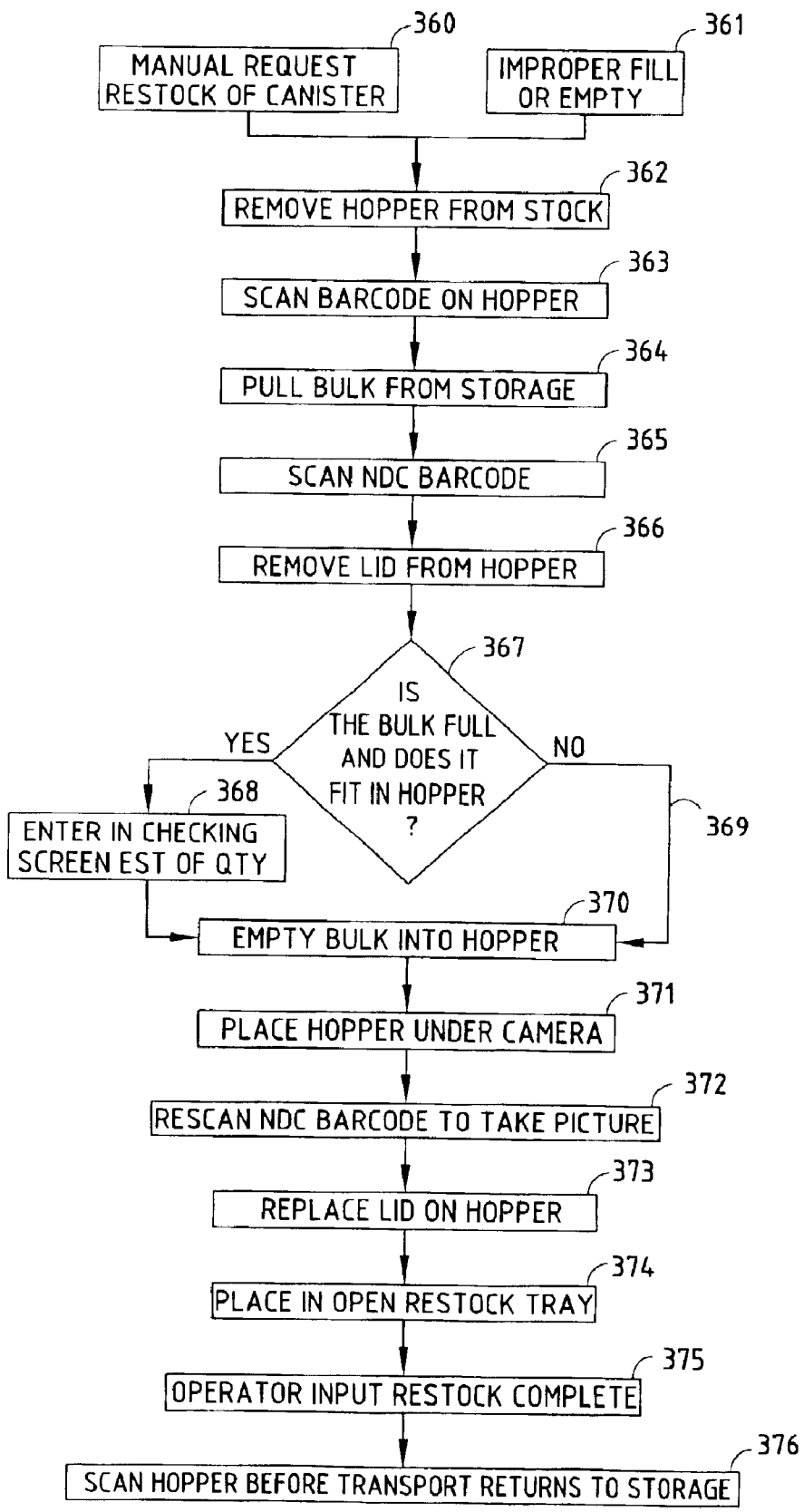

Three preferred methods are shown in FIGS. 36–38. Briefly, they are as follows. Nonetheless, it is contemplated that a number of different variations are possible, while still staying within the parameters of the present inventive concepts.

The method of FIG. 36 includes taking a prescription from a customer in a step 300, and entering the script in a computer in step 301. The pharmacist has the option of manually filling the prescription in step 302, or entering a request (i.e. "sending a string" to the computer) in a step 303. Upon receiving the request in step 304, the computer either returns the script to the pharmacist along a path 305 back to step 301/302 (such as if the computer doesn't recognize the script or can't fill the script), or sends the order to the database portion of the computer 57/controller 57C in step 306. When the order is received in step 306, the system in step 307 refers to the hopper database in step 307A to see if pills are available. If yes, the system in step 308 orders a vial to the pill-dispensing module in step 309 and also orders transport of a hopper of the required pills in step 310. Once the vial and hopper are in place in the pill-dispensing module, the system begins a fill routine in step 311. As part of the vial and hopper being in place, the computer checks the bar code on the prescription label applied to the vial and also the bar code on the hopper/storage unit to assure that the correct drug is being dispensed into the vial. Notably, a top of the vial stays open so that the pharmacist can look at the pills in the filled vial and at the prescription label to double check for accuracy and quality control purposes.

After the vial is filled in step 311, the computer updates the database in step 312. Then, the vial is transported to a holding station, where different prescriptions of the patient are collected. The image (step 313A) of the pill shape, size, type, and name are displayed along with a picture of the pill as the pharmacist picks up the filled vial, in step 313, and the pharmacist verifies the proper script. The fill information is sent to the host computer in step 314, and the billing information is generated in step 315. The prescription is then given to a customer/patient in step 316.

The fill routine shown in FIG. 37 is as follows. The completeness of the label and verification of the hopper contents are performed by a bar code reader in step 320. The computer then determines if there is a feed profile determined for the particular type, size, and shape of the pills being dispensed, in a step 321. If yes, the computer refers to the established feed profile in a step 322. If no, the computer refers to a new feed profile subroutine, in step 323. The new feed profile can begin at an established baseline, or can begin based on preprogrammed data relating to the shape, size, or type of pill being dispensed. Both steps 322 and 323 then lead to step 324, where the computer retrieves the feed profile and script count. The container gate (also called a "door" in the discussion above) is opened in step 325 by an actuator that engages the door and pushes it open. In step 326, the feed blocks or lift pins are adjusted to a desired height to set the hopper level pursuant to the profile desired. The pill counter begins counting pills as the pills drop, in a step 327. In a step 328, the computer repeatedly checks to determine if the pill count is within 5 of a final desired number of pills. If yes, the computer slows down the pill flow by deactivating one of the feed blocks (called a vibrator node, in the discussion above), in step 329. The computer checks to see if the pill count is achieved in step 330. If yes, the computer deactivates the feed blocks and closes the container door or gate in step 331, and sends an actual count signal to the checking database in a step 332. The computer then causes the filled vial to be transported to a holding station for pickup and final checking by the pharmacist in step 333.

If the pill count is not successfully achieved in step 330, (i.e. the pill count is within 5 but does not finish filling), the decision process moves to step 334 instead of to step 331. In step 334, a drop timer is activated. If the pill count is achieved before the timer times out, the computer goes directly to steps 331–333. If no, the process proceeds to step 335, where the computer repeatedly and periodically returns to step 330 until the timer times out. If the pill count is not achieved before the timer times out, the computer decision path moves to step 336 where it lowers the vibrational amplitudes of the vibrator nodes to a different setting, and if necessary, reactivates the second vibrator node in step 337. The computer then again returns to step 330 to determine if the last 5 pills have dropped.

If the count of pills is not within 5 in step 328, then progresses along the "no" decision line to box 328A and then to one of the class profiles in step 337 (class 4 or 5), step 338 (class 3), or step 339 (class 1 or 2). In step 337, the computer determines if class 5 is appropriate, and if yes, the computer sets the hopper to a lowest setting (in step 342) and sets the amplitude to a lowest setting (in step 343), and then returns to step 328. If the computer determines in step 337 that class 4 is appropriate, the computer proceeds in step 344 to determine if the hopper setting is above the profile setting. If yes, in step 345, the hopper is lowered. The computer then returns to step 328. If the computer determines in step 337 that class 4 is appropriate, and also determines in step 344 that the hopper setting is NOT above the profile setting, then the computer proceeds in step 346 to lower the amplitude setting. It then returns to step 338.

If in step 337, the computer moves to step 338 (i.e. class 3) and determines that the feed rate is appropriate, then the computer simply returns to step 328 and begins the cycle again.

If the computer moves to step 339 (i.e. class 1 or 2), and determines that class 2 is appropriate (line 348), the computer raises the hopper (step 349) and then proceeds back to the step 328.

If the computer moves to step 339 (i.e. class 1 or 2) and determines that class 1 is appropriate (line 350), then the computer checks to determine if the drop timer has exceeded its limit (step 351). If yes, the computer moves to deactivate the feed blocks and close the container gate (step 331), sends the actual count to the checking database (step 332) and proceed to vial transport (step 333). If no in step 351, then the computer checks to see if the hopper is at the maximum height in step 352. If yes, it lowers the hopper to a home position and then returns it to a maximum height in step 353. (In other words, it cycles the hopper up and down once to "break" any bunching and bridging of the pills on the track). If no, it raises the hopper and amplitude one setting in step 354. The computer then returns to step 328.

In the restock routing of FIG. 38, the system is entered by a manual request to restock a canister (also called a "storage unit" herein) (step 360) or by an improper fill or empty storage unit (step 361). From step 360 or 361, the computer sends a signal to remove the hopper from the storage location for restock in step 362. The barcode is scanned on the hopper in step 363, and the new bulk supply is pulled from storage in step 364. The barcode is scanned on the new supply/container of bulk pills in step 365. The lid is removed from the hopper of the storage unit in step 366, and it is determined whether the new pills from the new bulk supply will fit into the hopper in step 367. If not, the estimate of quantity added is entered in the computer in step 368. If the exact quantity of added pills is known, this is entered at line 369. The contents of the new bulk supply container are then put into the hopper of the storage unit in step 370. The hopper is placed under a camera in step 371, and the NDC bar code of the new bulk container is rescanned to take a picture in step 372. The lid is then replaced on the hopper of the storage container in step 373, and the storage unit is placed on the restock tray in step 374. The operator then inputs that the restock is complete in step 375. And the hopper is scanned before the transport/retriever returns the refilled storage unit to its storage location in the array of stored units (in step 376). The present refill procedure is highly efficient and accurate, and includes good quality control to prevent errors.

The present apparatus 40 is constructed to operate at a fast prescription/vial fill rate of at least about 110 prescriptions per hour, which is significantly faster than known competitive machines intended for use in retail environments. This speed is achieved in part based on the very high density of pills per total storage space. The speed of the present apparatus 40 is also due in part to the novel linear track, which "immediately" begins dropping pills when activated. (For example, many competitive apparatus have a rotating vibratory feeder where pills must be "lifted" (or moved vertically or slid long distances) as part of their pill singulation process, which takes time.) Notably, the short length of the present track also reduces degradation and "dust" from abraded pills, since the pills travel shortest distances. Also, the stored pills are more tightly sealed and protected over many known systems such that sanitation and cleanliness is improved.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A pill-dispensing apparatus for automatically dispensing solid pills, comprising:

a plurality of storage units for storing pills in bulk, each storage unit including an outer container, a track positioned in a bottom of the outer container, and a hopper movably positioned within the outer container for movement toward and away from the track to vary a size of a gap therebetwewn; and a pill-dispensing module including a dock for receiving and holding a selected one of the storage units, a drive unit for oscillating the track to motivate the pills along the track, a pill counter for counting pills dispensed from the track, and a lift for raising and lowering the hopper to vary a gap between the hopper and the track to control flow and to and to assist in motivating pills to fall from the hopper to the track.

2. The pill-dispensing apparatus defined in claim 1, including a mobile frame, the storage units being supported on the mobile frame, and including a retriever operable supported on the frame for retrieving a selected one of the storage units based on prescription information and for positioning the selected one storage unit in the pill-dispensing module.

3. The pill-dispensing apparatus defined in claim 2, including a bulk vial handler on the mobile frame for holding a vial under the pill-dispensing module for receiving the dispensed pills.

4. The pill-dispensing apparatus defined in claim 3, including a prescription information station including a computer operably connected to the retriever for receiving patient prescription information.

5. The pill-dispensing apparatus defined in claim 4, including a printer for printing a label for the vial and for applying the label to the vial.

6. The pill-dispensing apparatus defined in claim 5, including a control system for operating the pill-dispensing module, the retriever, the vial handler, and the printer.

7. The pill-dispensing apparatus defined in claim 1, including a vial handler for holding a vial under the pill-dispensing module for receiving the dispensed pills.

8. The pill-dispensing apparatus defined in claim 1, including a prescription information station including a computer operably connected to the pill-dispensing module for receiving patient prescription information.

9. The pill-dispensing apparatus defined in claim 1, wherein the vibrator includes first and second vibrator nodes that are independently controlled.

10. The pill-dispensing apparatus defined in claim 1, including a controller for operating the pill-dispensing module, the retriever, the vial handler, and the printer.

11. The pill-dispensing apparatus defined in claim 1, wherein the track comprises:

a solid member having a top surface defining a horizontal plane, the top surface having a groove formed therein that extends from an upstream end of the solid member across a middle section of the solid member to a downstream end of the solid member and further that extends to an edge of the solid member at the downstream end;

the groove in the downstream end defining a well-defined "V" shape with first angled side surfaces that are adapted to convey singulated pills one at a time off the edge of the downstream end, the groove in the upstream end defining an enlarged shape with second angled side surfaces shaped to store pills but also slidingly convey pills flowing onto the upstream end toward a center of the groove; and the groove in the middle section being formed from third angled side surfaces that extend at compound angles to the first and second angled side surfaces to form a transition pocket that redistributes bunched-up pills as the bunched-up pills travel from the upstream end into the middle section in order to unbunch the pills, and then centers and singulates the pills as the unbunched pills travel out of the transition pocket in the middle section to the downstream end.

12. The pill-dispensing apparatus defined in claim 1, including:

a mobile frame on wheels;

the plurality of storage units being movably stored on the frame;

an x-y-z direction retriever module on the frame for retrieving the storage units one at a time based on prescription information;

the pill-dispensing module also being supported on the frame, and including a dock for receiving and holding a selected one of the storage units and for dispensing pills from the selected one storage unit, the retriever being adapted to position the selected one storage unit in the pill-dispensing module for dispensing pills and then being adapted to replace the selected one storage unit in its storage position on the frame;

a vial handler module on the frame for holding a vial under the pill-dispensing module for receiving the dispensed pills; and a controller for operating the pill-dispensing module, the retriever module, and the vial handler module.

13. A combination including a pill-dispensing apparatus as defined in claim 1, and a countertop and countertop support adapted to position the countertop above a floor surface at a height suitable for use by a pharmacist standing and working adjacent the countertop, the countertop having a top surface suitable for handling pills and filling prescriptions, and further the opposing sides of the countertop being open so that the pharmacist can communicate with and give prescriptions to customers on a side of the countertop opposite from the pharmacist; the pill-dispensing apparatus including a retriever for selecting one of the storage units, a dispensing station for dispensing pills from the selected storage unit, a vial handler for collecting the dispensed pills, all of which are positioned under the countertop.

14. A pill-dispensing apparatus for automatically dispensing solid pills, comprising:

an outer container;

a track positioned at a bottom of the outer container;

a hopper movably positioned within the outer container for movement toward and away from the track;

a dock for holding the storage unit;

an oscillator for vibrating the track to motivate the pills along the track; and a lift for lifting the hopper to adjustably increase a gap between the track and the hopper when pills bridge up and stop moving along the track.

15. A pill-dispensing apparatus for automatically dispensing solid pills, comprising:

a frame with storage locations;

a plurality of storage units movably stored in respective ones of the storage locations, the storage units being adapted to hold pills in bulk, the storage units having a depth and being arranged in first and second vertical parallel planes with a space therebetween at least as deep as the depth of the storage units, the storage units each having a track associated therewith;

an x-y-z direction retriever module operably mounted on the frame for movement in the space, the retriever module including a carrier adapted to carry a selected one of the storage units, the retriever further including first, second and third actuators operable to move the retriever in x, y, and z orthogonal directions, respectively, and further including a coupler operable to grip the selected one storage unit as the selected one storage unit is pulled from its respective storage location onto the carrier;

a pill-dispensing module on the frame, including a dock for receiving and holding the selected one of the storage units and a pill-dispensing mechanism for dispensing pills from the selected one storage unit, the pill-dispensing mechanism including a vibrator with first and second nodes that engage the track at spaced apart locations for vibrating portions of the track with dissimilar vibration patterns; and a controller for controlling the first, second, and third actuators, the gripper, and the pill-dispensing mechanism.

16. A pill-dispensing apparatus for automatically dispensing solid pills, comprising:

a hopper;

a track positioned at a bottom of the hopper;

one of the hopper and the track being supported for movement toward and away from the other of the hopper and the track to vary a gap between the hopper and the track to control pill flow from the hopper; and an oscillator including first and second nodes engaging the track for vibrating different portions of the track with separately-generated vibrations to motivate the pills along the track.

17. The pill-dispensing apparatus for automatically dispensing solid pills defined in claim 16, wherein:

the first and second nodes are oriented at dissimilar angles for vibrating different portions of the track with vibrations at dissimilar angles to motivate the pills along the track.

18. The pill-dispensing apparatus for automatically dispensing solid pills defined in claim 17, wherein the separately-generated vibrations are at different frequencies.

19. The pill-dispensing apparatus for automatically dispensing solid pills defined in claim 16, wherein the first and second nodes vibrate with the same frequency to motivate the pills along the track.

20. The pill-dispensing apparatus for automatically dispensing solid pills as defined in claim 16, wherein the oscillator frequency may be adjusted within a range to motivate the pills along the track at different rates.

* * * * *

UNITED STATES PATENT AND TRADEMARK OFFICE
CERTIFICATE OF CORRECTION

PATENT NO. : 7,210,598 B2
APPLICATION NO. : 10/160970
DATED : May 1, 2007
INVENTOR(S) : William O. Gerold and William J. Gerold It is certified that error appears in the above-identified patent and that said Letters Patent is hereby corrected as shown below:

On the Title Page Item (54) and Col. 1, line 1

"Authomated" should be -- Automated --;

Col. 16, claim 1, line 22

"therebetwewn" should be -- therebetween --;

Col. 16, claim 1, line 29

Delete "and to" (second occurrence);

Col. 16, claim 2, line 33

"operable" should be -- operably --;

Col. 17, claim 13, line 56

After "unit," insert -- and --.

Signed and Sealed this

Fourteenth Day of August, 2007

JON W. DUDAS
*Director of the United States Patent and Trademark Office*